(12) United States Patent
Lu et al.

(10) Patent No.: US 10,137,777 B2
(45) Date of Patent: Nov. 27, 2018

(54) SYSTEMS AND METHODS FOR VEHICLE SYSTEM CONTROL BASED ON PHYSIOLOGICAL TRAITS

(71) Applicant: GM GLOBAL TECHNOLOGY OPERATIONS LLC, Detroit, MI (US)

(72) Inventors: Peng Lu, Troy, MI (US); Xiaosong Huang, Novi, MI (US); Joseph F. Szczerba, Grand Blanc, MI (US); Tricia E. Neiiendam, Oakland Township, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 71 days.

(21) Appl. No.: 15/410,582

(22) Filed: Jan. 19, 2017

(65) Prior Publication Data

US 2017/0129335 A1 May 11, 2017

Related U.S. Application Data

(63) Continuation-in-part of application No. 15/342,451, filed on Nov. 3, 2016.
(Continued)

(51) Int. Cl.
*B60K 28/06* (2006.01)
*A61B 5/00* (2006.01)
(Continued)

(52) U.S. Cl.
CPC .......... *B60K 28/066* (2013.01); *A61B 5/681* (2013.01); *A61B 5/6803* (2013.01); *A61B 5/6804* (2013.01); *B60H 1/00964* (2013.01); *B60K 28/06* (2013.01); *B60W 50/10* (2013.01); *G01S 19/13* (2013.01); *G05D 1/0061* (2013.01); *G06F 1/163* (2013.01); *G06F 1/1684* (2013.01);
(Continued)

(58) Field of Classification Search
CPC .. B60K 28/06; G05D 1/0061; B60H 1/00964; A61B 5/6803; A61B 5/6804; A61B 5/681; B60W 50/10; G06F 1/163; G06F 1/1684; G06F 1/1694; G06F 3/017; G06F 19/00

See application file for complete search history.

(56) References Cited

U.S. PATENT DOCUMENTS 8,072,309 B2   12/2011   Kraimer et al.
8,214,098 B2   7/2012    Murray
(Continued)

FOREIGN PATENT DOCUMENTS

WO   2014089696 A1   6/2014

OTHER PUBLICATIONS

Gareffa, Peter, "Gestures Find Their Way Into Automotive Control Systems," Mar. 17, 2014, pp. 1-3, Edmunds Inc.
(Continued)

*Primary Examiner* — Mussa A Shaawat
(74) *Attorney, Agent, or Firm* — Lorenz & Kopf, LLP

(57) ABSTRACT

Systems and methods are provided for controlling a vehicle based on a physiological trait. The method includes: receiving physiological data from one or more physiological sensors; processing the received physiological data, by a processor, to determine one or more physiological conditions; and based on the determined physiological condition, outputting one or more control signals to a vehicle system to control an operation of the vehicle system.

17 Claims, 8 Drawing Sheets

Related U.S. Application Data

(60) Provisional application No. 62/250,180, filed on Nov. 3, 2015, provisional application No. 62/287,422, filed on Jan. 26, 2016.

(51) Int. Cl.
| | | |
|---|---|---|
| *B60H 1/00* | (2006.01) | |
| *G01S 19/13* | (2010.01) | |
| *G05D 1/00* | (2006.01) | |
| *G06F 19/00* | (2018.01) | |
| *G16H 10/60* | (2018.01) | |
| *B60W 50/10* | (2012.01) | |
| *G06F 1/16* | (2006.01) | |
| *G06F 3/01* | (2006.01) | |

(52) U.S. Cl.
CPC ............ *G06F 1/1694* (2013.01); *G06F 3/017* (2013.01); *G06F 19/00* (2013.01); *G06F 19/324* (2013.01); *G16H 10/60* (2018.01)

(56) References Cited

U.S. PATENT DOCUMENTS

| | | |
|---|---|---|
| 8,942,881 B2 | 1/2015 | Hobbs et al. |
| 8,965,460 B1 | 2/2015 | Rao et al. |
| 9,283,905 B2 | 3/2016 | Herthan |
| 9,346,470 B2 | 5/2016 | Mittermeier |
| 9,355,236 B1 | 5/2016 | Kratz et al. |
| 9,575,481 B2 | 2/2017 | Newman et al. |
| 9,576,285 B2 | 2/2017 | Zhou |
| 9,580,046 B2 | 2/2017 | Luu |
| 9,613,197 B2 | 4/2017 | Pathangay et al. |
| 9,639,685 B2 | 5/2017 | Anderson |
| 9,777,528 B2 | 10/2017 | Elie |
| 9,811,648 B2 | 11/2017 | Choi et al. |
| 9,818,246 B2 | 11/2017 | Elie |
| 2002/0152010 A1 | 10/2002 | Colmenarez |
| 2006/0145825 A1 | 7/2006 | Me Call |
| 2010/0185341 A1 | 7/2010 | Wilson |
| 2011/0187492 A1 | 8/2011 | Newman et al. |
| 2011/0286676 A1 | 11/2011 | El Dokor |
| 2012/0291073 A1 | 11/2012 | Friedman |
| 2013/0104227 A1 | 4/2013 | Dow et al. |
| 2013/0138714 A1 | 5/2013 | Ricci |
| 2014/0120932 A1 | 5/2014 | Carmon |
| 2014/0136024 A1 | 5/2014 | Herthan |
| 2014/0139422 A1 | 5/2014 | Mistry et al. |
| 2014/0194061 A1 | 7/2014 | Fine |
| 2014/0320399 A1 | 10/2014 | Kim et al. |
| 2014/0379175 A1 | 12/2014 | Mittermeier |
| 2015/0028996 A1 | 1/2015 | Agrafioti et al. |
| 2015/0032473 A1 | 1/2015 | Sadrieh |
| 2015/0042454 A1 | 2/2015 | Lee |
| 2015/0048927 A1 | 2/2015 | Simmons |
| 2015/0074797 A1 | 3/2015 | Choi et al. |
| 2015/0077235 A1 | 3/2015 | Pisz |
| 2015/0081169 A1 | 3/2015 | Pisz |
| 2015/0145646 A1 | 5/2015 | Seino |
| 2015/0156567 A1 | 6/2015 | Oliver et al. |
| 2015/0161836 A1 | 6/2015 | Park |
| 2015/0186609 A1 | 7/2015 | Utter, II |
| 2015/0220109 A1 | 8/2015 | von Badinski et al. |
| 2015/0220157 A1 | 8/2015 | Marggraff et al. |
| 2015/0242015 A1 | 8/2015 | Cho et al. |
| 2015/0245186 A1 | 8/2015 | Park et al. |
| 2015/0248235 A1 | 9/2015 | Offenberg et al. |
| 2015/0277559 A1 | 10/2015 | Vescovi et al. |
| 2015/0293592 A1 | 10/2015 | Cheong et al. |
| 2015/0332031 A1 | 11/2015 | Mistry et al. |
| 2015/0332532 A1 | 11/2015 | Lee |
| 2015/0336521 A1 | 11/2015 | Tofilescu et al. |
| 2015/0350413 A1 | 12/2015 | Ma |
| 2016/0007849 A1 | 1/2016 | Krueger |
| 2016/0030835 A1 | 2/2016 | Argiro |
| 2016/0037251 A1 | 2/2016 | Daniels |
| 2016/0061613 A1 | 3/2016 | Jung |
| 2016/0070360 A1 | 3/2016 | Chehade et al. |
| 2016/0085958 A1 | 3/2016 | Kang |
| 2016/0127900 A1 | 5/2016 | Archibald et al. |
| 2016/0134737 A1 | 5/2016 | Pulletikurty |
| 2016/0187992 A1 | 6/2016 | Yamamoto |
| 2016/0188181 A1 | 6/2016 | Smith |
| 2016/0223577 A1 | 8/2016 | Klosinski, Jr. et al. |
| 2016/0248995 A1 | 8/2016 | Mullins et al. |
| 2016/0257198 A1 | 9/2016 | Buttolo et al. |
| 2016/0313798 A1 | 10/2016 | Connor |
| 2016/0347280 A1* | 12/2016 | Daman .................. H04W 4/70 |
| 2016/0378427 A1 | 12/2016 | Sharma et al. |
| 2016/0378963 A1 | 12/2016 | Anderson |
| 2017/0011210 A1 | 1/2017 | Cheong et al. |
| 2017/0021728 A1 | 1/2017 | Wild |
| 2017/0031446 A1* | 2/2017 | Clark .................... B64C 39/024 |
| 2017/0086072 A1 | 3/2017 | Mao et al. |
| 2017/0092232 A1 | 3/2017 | Mullins et al. |
| 2017/0102697 A1 | 4/2017 | Hassan et al. |
| 2017/0105101 A1 | 4/2017 | Santavicca |
| 2017/0147074 A1 | 5/2017 | Buttolo |
| 2017/0185103 A1 | 6/2017 | Kim et al. |
| 2017/0225690 A1 | 8/2017 | Elnajjar et al. |
| 2018/0096546 A1 | 4/2018 | Bartels |

OTHER PUBLICATIONS

"Keyless Entry System," Nartron, https://www.nartron.com/keyless_entry_system.pdf.

Khazan, Olga, "Mapping How Emotions Manifest in the Body," Dec. 30, 2013, The Atlantic.

* cited by examiner

SYSTEMS AND METHODS FOR VEHICLE SYSTEM CONTROL BASED ON PHYSIOLOGICAL TRAITS

CROSS-REFERENCE TO RELATED APPLICATIONS

This application claims the benefit of U.S. Provisional Application No. 62/287,422, filed on Jan. 26, 2016, and is a continuation-in-part of U.S. application Ser. No. 15/342, 451, filed on Nov. 3, 2016, which claims the benefit of U.S. Provisional Application No. 62/250,180, filed on Nov. 3, 2015. Each of the above referenced applications is incorporated herein by reference.

TECHNICAL FIELD

The present disclosure generally relates to vehicles and more particularly relates to systems and methods for controlling vehicle systems based on one or more physiological traits of a user.

BACKGROUND

An autonomous vehicle is a vehicle that is capable of sensing its environment and navigating with little or no user input. An autonomous vehicle senses its environment using sensing devices such as radar, lidar, image sensors, and the like. The autonomous vehicle system further uses information from global positioning systems (GPS) technology, navigation systems, vehicle-to-vehicle communication, vehicle-to-infrastructure technology, and/or drive-by-wire systems to navigate the vehicle.

Vehicle automation has been categorized into numerical automotive levels ranging from Zero, corresponding to no automation with full human control, to Five, corresponding to full automation with no human control. Various automated driver-assistance systems, such as cruise control, adaptive cruise control, and parking assistance systems correspond to lower automation levels, while true "driverless" vehicles correspond to higher automation levels.

A vehicle may have one or more automated driver-assistance systems of a lower automation level, which requires user input for operation. In certain instances, however, the user may not be able to provide direct input, for example, due to a current driving situation or a health condition associated with the user. In other instances, the user may want to simply have the convenience to operate the vehicle or a vehicle system indirectly without deliberate user action.

Accordingly, it is desirable to provide systems and methods for controlling a vehicle system without deliberate user input. It is further desirable to provide systems and methods for controlling a vehicle system based on one or more physiological traits of a user. Furthermore, other desirable features and characteristics of the present disclosure will become apparent from the subsequent detailed description and the appended claims, taken in conjunction with the accompanying drawings and the foregoing technical field and background.

SUMMARY

Systems and methods are provided for controlling a vehicle. In one embodiment, a method for controlling a vehicle based on a physiological trait includes: receiving physiological data from one or more physiological sensors; processing the received physiological data, by a processor, to determine one or more physiological conditions; and based on the determined physiological condition, outputting one or more control signals to a vehicle system to control an operation of the vehicle system.

In various embodiments, the method further includes: processing the received physiological data, by the processor, to generate a baseline physiological reading; processing subsequently received physiological data, by the processor, to determine a physiological change; and based on the determined physiological change, outputting one or more control signals to the vehicle system to control the operation of the vehicle system. The method further includes: retrieving a setting associated with the determined physiological change, wherein outputting the one or more control signals to the vehicle system is based on the setting. The setting is a user defined setting or a predefined default setting. The method further includes: outputting a message to an external authority system based on the determined physiological condition. The method also includes: outputting at least a notification and a GPS location of the vehicle based on the determined physiological condition. The method includes outputting a prompt based on the determined physiological condition; and determining, by the processor, whether a user response has been received, wherein the outputting one or more control signals to the vehicle system is based on the user response. The determining, by the processor, whether the user response has been received further includes: receiving sensor data from one or more response sensors; processing the sensor data to determine whether a gesture has been made by the user; and determining the response has been received based on the determination of the gesture.

In one embodiment, a system for controlling a vehicle based on a physiological trait is provided. The system includes a source of physiological data regarding a user of the vehicle. The system also includes a control module having a processor that processes the physiological data and outputs at least one of one or more control signals to a vehicle control system to operate the vehicle autonomously based on the physiological data and one or more control signals to the vehicle control system to command one or more of an HVAC system, a seat system, an infotainment system, a lock system, a light system, a window system and an alarm system based on the physiological data.

The source of physiological data is a personal device associated with the user. The processor processes the physiological data to generate a baseline physiological reading, processes subsequently received physiological data to determine a physiological change and outputs the one or more control signals to the vehicle control system based on the determined physiological change. The processor retrieves a setting associated with the determined physiological change, and outputs the one or more control signals to the vehicle control system is based on the setting. The setting is a user defined setting or a predefined default setting. The processor processes the received physiological data and determines one or more physiological conditions, and outputs one or more control signals to the vehicle control system based on the determined physiological condition. The processor outputs a message to an external authority system based on the determined physiological condition. The processor outputs at least a notification and a GPS location of the vehicle based on the determined physiological condition. The processor outputs a prompt based on the determined physiological condition, determines whether a user response has been received and the control module outputs the one or more control signals to the at least one vehicle system based on the user response. The processor determines whether the user response has been received based on sensor data received from one or more response sensors, and the processor processes the sensor data to determine whether a gesture has been made by the user. The processor determines the user response has been received based on the determination of the gesture.

In one embodiment, a wearable physiological device is provided. The wearable physiological device includes at least one physiological sensor that observes at least one physiological condition associated with a wearer of the physiological device and generates sensor signals based thereon. The wearable physiological device also includes a control module having a processor that processes the sensor signals and outputs the sensor signals to a system associated with a vehicle.

The wearable physiological device is a portable electronic device selected from the group comprising: a watch, a ring, an earring, a bracelet, a cufflink, a necklace, a tie, glasses, chest band, smart clothes and combinations thereof.

DESCRIPTION OF THE DRAWINGS

The exemplary embodiments will hereinafter be described in conjunction with the following drawing figures, wherein like numerals denote like elements, and wherein.

DETAILED DESCRIPTION

The following detailed description is merely exemplary in nature and is not intended to limit the application and uses. Furthermore, there is no intention to be bound by any expressed or implied theory presented in the preceding technical field, background, brief summary or the following detailed description. As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the vehicle system described herein is merely one exemplary embodiment of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

Figure 1:
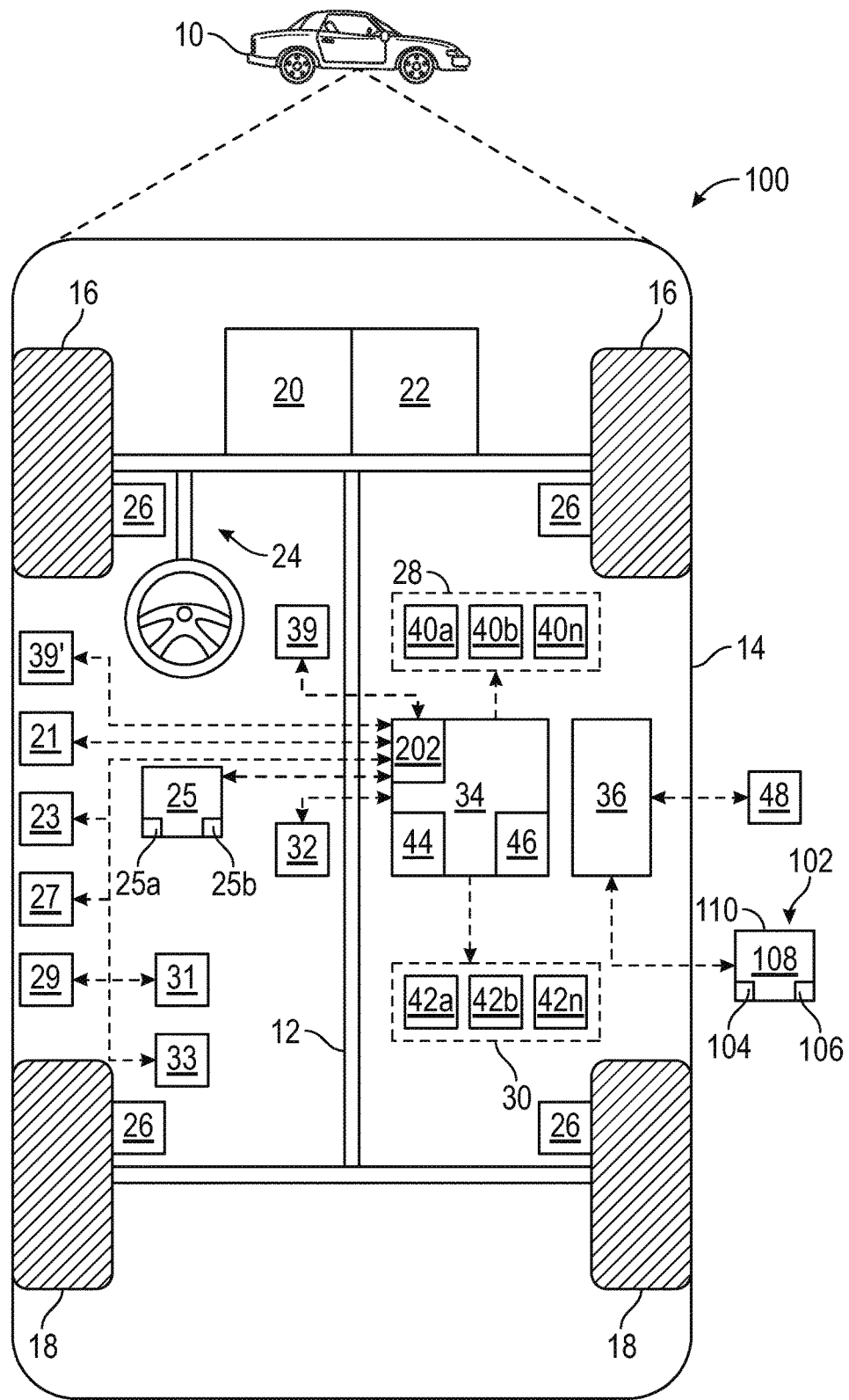
FIG. 1 is a functional block diagram illustrating an autonomous vehicle having a physiological control system, in accordance with various embodiments.

With reference to FIG. 1, a physiological control system shown generally at 100 is associated with a vehicle 10 in accordance with various embodiments. In general, the physiological control system 100 receives an input from a physiological monitoring device 102 and intelligently controls the vehicle 10 based thereon.

As depicted in FIG. 1, the vehicle 10 generally includes a chassis 12, a body 14, front wheels 16, and rear wheels 18. The body 14 is arranged on the chassis 12 and substantially encloses components of the vehicle 10. The body 14 and the chassis 12 may jointly form a frame. The wheels 16-18 are each rotationally coupled to the chassis 12 near a respective corner of the body 14.

In various embodiments, the vehicle 10 is an autonomous vehicle and the physiological control system 100 is incorporated into or associated with the autonomous vehicle 10 (hereinafter referred to as the autonomous vehicle 10). The autonomous vehicle 10 is, for example, a vehicle that is automatically controlled to carry passengers from one location to another. The autonomous vehicle 10 is depicted in the illustrated embodiment as a passenger car, but it should be appreciated that any other vehicle including motorcycles, trucks, sport utility vehicles (SUVs), recreational vehicles (RVs), marine vessels, aircraft, etc., can also be used. In an exemplary embodiment, the autonomous vehicle 10 is a so-called Level Three, Level Four or Level Five automation system. A Level Three system indicates "conditional automation," referring to the driving mode-specific performance by an automated driving system of all aspects of the dynamic driving task with the expectation that the human driver will respond appropriately to a request to intervene. A Level Four system indicates "high automation," referring to the driving mode-specific performance by an automated driving system of all aspects of the dynamic driving task, even if a human driver does not respond appropriately to a request to intervene. A Level Five system indicates "full automation," referring to the full-time performance by an automated driving system of all aspects of the dynamic driving task under all roadway and environmental conditions that can be managed by a human driver. It will be noted, however, that physiological control system 100 may also be coupled to or incorporated with a lower level automation system, if desired.

As shown, the vehicle 10 generally includes a propulsion system 20, a transmission system 22, a steering system 24, a brake system 26, a sensor system 28, an actuator system 30, at least one data storage device 32, at least one controller 34, and a communication system 36. The propulsion system 20 may, in various embodiments, include an internal combustion engine, an electric machine such as a traction motor, and/or a fuel cell propulsion system. The transmission system 22 is configured to transmit power from the propulsion system 20 to the wheels 16-18 according to selectable speed ratios. According to various embodiments, the transmission system 22 may include a step-ratio automatic transmission, a continuously-variable transmission, or other appropriate transmission. The brake system 26 is configured to provide braking torque to the wheels 16-18 and/or the transmission system 22. The brake system 26 may, in various embodiments, include friction brakes, brake by wire, a regenerative braking system such as an electric machine, and/or other appropriate braking systems. The steering system 24 influences the course of travel by the autonomous vehicle 10, for example by adjusting a position of the wheels 16-18. While depicted as including a steering wheel for illustrative purposes, in some embodiments contemplated within the scope of the present disclosure, the steering system 24 may not include a steering wheel.

The vehicle 10 also generally includes one or more user comfort and convenience systems, including, but not limited to, a heat ventilation and cooling (HVAC) system 21, a seat system 23, an infotainment system 25, a lock system 27, a lighting system 29, a window system 31, an alarm system 33, etc. The HVAC system 21, in various embodiments, includes a motor that is coupled to a blower, and the motor is actuated to drive the blower to direct air through a condenser (for cooled air) and/or a heater (for heated air) to arrive at a desired ambient air temperature within the vehicle 10. The condenser and the heater may also be actuated to cool or heat the air stream from the blower. In various embodiments, the seat system 23 is associated with one or more seating surfaces or seats of the vehicle 10 and includes one or more motors that are actuated to move the respective seat in various directions, including, but not limited to, fore and aft, up and down, tilt, etc. The seat system 23 may also include a motor that is actuated to provide increasing or decreasing lumbar support, and may also include a heater coil that is actuated to provide heat output for the one or more seats (e.g. seat warmer). In various embodiments, the seat system 23 may also include a cooling control valve, which is actuated to direct cooled air from the HVAC system 21 into the one or more seats to cool the seating surfaces (e.g. seat cooler).

In various embodiments, the infotainment system 25 includes a display 25a and one or more input devices 25b. The infotainment system 25 may also include other user entertainment options, including, but not limited to, a radio, DVD, etc. The infotainment system 25 is in communication with the physiological control system 100, and provides input, via a user's interaction with the one or more input devices 25b to the physiological control system 100. The display 25a generally comprises any display, which may be implemented in an instrument panel of the vehicle 10, such as a flat panel display, curved or other shape, or projection display, 3D virtual display and so on. The display 25a comprises any suitable technology for displaying information, including, but not limited to, a liquid crystal display (LCD), organic light emitting diode (OLED), plasma, or a cathode ray tube (CRT). The input device 25b comprise any device to receive input and/or commands from the user (e.g. wearable device, gesture detecting device, microphone, buttons, keyboard, etc.), and the input device 25b may comprise a touchscreen layer associated with the display 25a.

The lock system 27, in various embodiments, includes one or more lock actuators, which are operable to lock and unlock a respective one or more doors associated with the vehicle 10. It should be noted that the lock system 27 may also include one or more lock actuators that are operable to lock and unlock a tailgate or cargo access panel associated with the vehicle 10. In certain embodiments, the lock system 27 may also include one or more latch actuators, which are operable to unlatch or latch a respective one of the one or more doors, tailgate or cargo access panel associated with the vehicle 10.

The lighting system 29 includes one or more light output devices within a cabin of the vehicle 10 or external to the cabin of the vehicle 10 (e.g. headlights and tail lights). In various embodiments, the lighting system 29 may be actuated to illuminate the one or more lights external to the cabin of the vehicle, or to flash the lights external to the cabin of the vehicle 10. In addition, the lighting system 29 may be actuated to change a color of light output in the cabin of the vehicle 10 or to illuminate the cabin of the vehicle 10. In various embodiments, the window system 31 includes one or more motors, which are each associated with a respective drive system of a window of the vehicle 10. The one or more motors are actuated to move the respective window between an opened position and a closed position. In various embodiments, the alarm system 33 includes a siren or other output device is actuated to generate a loud noise.

The sensor system 28 includes one or more sensors or sensing devices 40a, 40b . . . 40n that sense observable conditions of the exterior environment, as well as the interior environment and/or operating state of the autonomous vehicle 10. The sensing devices 40a, 40b . . . 40n can include, but are not limited to, radars, lidars, global positioning systems, optical cameras, thermal cameras, ultrasonic sensors, and/or other sensors, communication link devices or GPS antennas. The actuator system 30 includes one or more actuator devices 42a, 42b . . . 42n that control one or more vehicle features, components, systems and/or functions such as, but not limited to, the propulsion system 20, the transmission system 22, the steering system 24, the brake system 26, the HVAC system 21, the seat system 23, the infotainment system 25, the lock system 27, the lighting system 29, the window system 31 and the alarm system 33.

The data storage device 32 stores data for use in automatically controlling the autonomous vehicle 10. In various embodiments, the data storage device 32 stores defined maps of the navigable environment. In various embodiments, the defined maps may be predefined by and obtained from a remote system (described in further detail with regard to FIG. 2). For example, the defined maps may be assembled by the remote system and communicated to the autonomous vehicle 10 (wirelessly and/or in a wired manner) and stored in the data storage device 32. As can be appreciated, the data storage device 32 may be part of the controller 34, separate from the controller 34, or part of the controller 34 and part of a separate system.

The controller 34 includes at least one processor 44 and a computer readable storage device or media 46. The processor 44 can be any custom made or commercially available processor, a central processing unit (CPU), a graphics processing unit (GPU), an auxiliary processor among several processors associated with the controller 34, a semiconductor based microprocessor (in the form of a microchip or chip set), a macroprocessor, any combination thereof, or generally any device for executing instructions. The computer readable storage device or media 46 may include volatile and nonvolatile storage in read-only memory (ROM), random-access memory (RAM), and keep-alive memory (KAM), for example. KAM is a persistent or non-volatile memory that may be used to store various operating variables while the processor 44 is powered down. The computer-readable storage device or media 46 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 34 in controlling the autonomous vehicle 10.

The instructions may include one or more separate programs, each of which comprises an ordered listing of executable instructions for implementing logical functions. The instructions, when executed by the processor 44, receive and process signals from the sensor system 28, perform logic, calculations, methods and/or algorithms for automatically controlling the components of the autonomous vehicle 10, and generate control signals to the actuator system 30 to automatically control the components of the autonomous vehicle 10 based on the logic, calculations, methods, and/or algorithms. Although only one controller 34 is shown in FIG. 1, embodiments of the autonomous vehicle 10 can include any number of controllers 34 that communicate over any suitable communication medium or a combination of communication mediums and that cooperate to process the sensor signals, perform logic, calculations, methods, and/or algorithms, and generate control signals to automatically control features of the autonomous vehicle 10.

In various embodiments, one or more instructions of the controller 34 are embodied in the physiological control system 100 and, when executed by the processor 44, cause the processor 44 to process an input received from the physiological monitoring device 102 and output one or more control signals to the actuator system 30 to control the one or more vehicle features, components, systems and/or functions of the vehicle 10 based on the input received from the physiological monitoring device 102. For example, the processor 44 may process the input received from the physiological monitoring device 102 and output one or more control signals to the actuator system 30 to autonomously drive the vehicle 10 based on one or more sensor signals or the received input from the physiological monitoring device 102. The processor 44 may process the input received from the physiological monitoring device 102 and output one or more control signals to the actuator system 30 to control one or more of the HVAC system 21, the seat system 23, the infotainment system 25, the lock system 27, the lighting system 29, the window system 31 and the alarm system 33.

Figure 2:
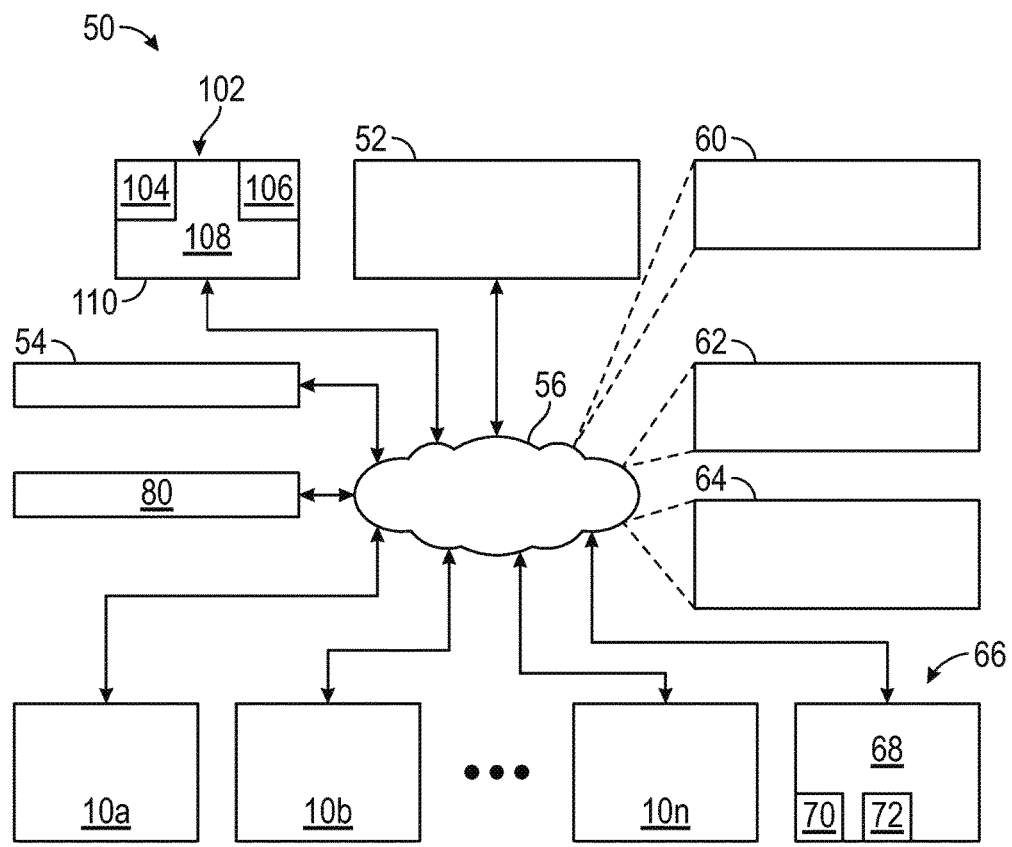
FIG. 2 is a functional block diagram illustrating a transportation system having one or more autonomous vehicles of FIG. 1, in accordance with various embodiments.

The communication system 36 is configured to wirelessly communicate information to and from other entities 48, such as but not limited to, other vehicles ("V2V" communication), infrastructure ("V2I" communication), remote systems, and/or personal devices (described in more detail with regard to FIG. 2). In an exemplary embodiment, the communication system 36 is a wireless communication system configured to communicate via a wireless local area network (WLAN) using IEEE 802.11 standards, Bluetooth® or by using cellular data communication. However, additional or alternate communication methods, such as a dedicated short-range communications (DSRC) channel, are also considered within the scope of the present disclosure. DSRC channels refer to one-way or two-way short-range to medium-range wireless communication channels specifically designed for automotive use and a corresponding set of protocols and standards. The communication system 36 may also be configured to encode data or generate encoded data. The encoded data generated by the communication system 36 may be encrypted. A security key may be utilized to decrypt and decode the encoded data, as is appreciated by those skilled in the art. The security key may be a "password" or other arrangement of data, finger print, eye fingerprint, face recognition, or DNA recognition that permits the encoded data to be decrypted.

The vehicle 10 also includes one or more response sensors 39. The one or more response sensors 39 are in communication with the physiological control system 100 embodied within the controller 34. The one or more response sensors 39 observe a user of the vehicle 10 and generate sensor signals based thereon. In various embodiments, the one or more response sensors 39 observe a response or gesture of the user, and generate sensor signals based thereon. For example, the one or more response sensors 39 include, but are not limited to, a camera, radar, wired gloves, and wearable devices, including, but not limited to, portable electronic devices in the form of watches, rings, earrings, bracelets, cufflinks, necklaces, ties, glasses, chest band, smart clothes, etc., which are configured to observe one or more gestures or motions made by the user. Based on the sensor signals from the response sensors 39, the physiological control system 100 controls one or more of the systems of the vehicle 10, such as the HVAC system 21, the seat system 23, the infotainment system 25, the lock system 27, the lighting system 29, the window system 31, the alarm system 33 and a autonomous driving system 200. Stated another way, one or more movements or gestures of the user of the vehicle 10 is observed and processed by the physiological control system 100 to control one or more of the vehicle systems or the operation of the vehicle 10 itself.

In some embodiments, the response sensors 39 include at least one camera 39' and at least one range sensor. The range sensor may include a short-range radar (SRR), an ultrasonic sensor, a long-range RADAR, a Light Detection And Ranging (LiDAR) sensor. The camera 39' and the range sensor may comprise one of the sensors 40a, 40b . . . 40n of the sensor system 28. The camera 39' shown schematically represents one or multiple cameras positioned in any appropriate or suitable location of the vehicle 10, such as at vehicle side mirrors, adjacent or at door handles, at a rear decklid, facing out from vehicle head and/or tail lamps, within a cabin of the vehicle 10, etc. Each camera 39' is configured to sense presence of a user and, in some embodiments, user motion. Each is movable, such automatically moved by actuator controlled by a computer-based system 700 (FIG. 8) or controller 34 to track a user moving near the vehicle. Cameras can be used in conjunction with other sensors, such as laser-motion detecting sensors, to recognize user gestures. Sensors sensing user motion, including gestures, may be oriented in any of a variety of directions without departing from the scope of the present disclosure.

In one embodiment, the response sensor 39 is the user device 54. In this embodiment, the user device 54 is configured with at least one sensor, such as a RADAR based motion detector, to detect user movements. The user device 54 may include any appropriate components for sensing user gestures or movement, such as camera components, an inertial-momentum unit (IMU) having one or more accelerometers and transmits the sensed user gestures or movement to the vehicle 10 via the communication network 56.

With reference now to FIG. 2, in various embodiments, the autonomous vehicle 10 described with regard to FIG. 1 may be suitable for use in the context of a taxi or shuttle system in a certain geographical area (e.g., a city, a school or business campus, a shopping center, an amusement park, an event center, or the like) or may simply be managed by a remote system. For example, the autonomous vehicle 10 may be associated with an autonomous vehicle based remote transportation system. FIG. 2 illustrates an exemplary embodiment of an operating environment shown generally at 50 that includes an autonomous vehicle based remote transportation system 52 that is associated with one or more autonomous vehicles 10a, 10b . . . 10n as described with regard to FIG. 1. In various embodiments, the operating environment 50 further includes one or more user devices 54, a remote physiological processing system 66, one or more physiological monitoring devices 102 and one or more external authority systems 80 that communicate with the autonomous vehicle 10 and/or the remote transportation system 52 via a communication network 56.

The communication network 56 supports communication as needed between devices, systems, and components supported by the operating environment 50 (e.g., via tangible communication links and/or wireless communication links). For example, the communication network 56 can include a wireless carrier system 60 such as a cellular telephone system that includes a plurality of cell towers (not shown), one or more mobile switching centers (MSCs) (not shown), as well as any other networking components required to connect the wireless carrier system 60 with a land communications system. Each cell tower includes sending and receiving antennas and a base station, with the base stations from different cell towers being connected to the MSC either directly or via intermediary equipment such as a base station controller. The wireless carrier system 60 can implement any suitable communications technology, including for example, digital technologies such as CDMA (e.g., CDMA2000), LTE (e.g., 4G LTE or 5G LTE), GSM/GPRS, or other current or emerging wireless technologies. Other cell tower/base station/MSC arrangements are possible and could be used with the wireless carrier system 60. For example, the base station and cell tower could be co-located at the same site or they could be remotely located from one another, each base station could be responsible for a single cell tower or a single base station could service various cell towers, or various base stations could be coupled to a single MSC, to name but a few of the possible arrangements.

Apart from including the wireless carrier system 60, a second wireless carrier system in the form of a satellite communication system 64 can be included to provide unidirectional or bi-directional communication with the autonomous vehicles 10a, 10b . . . 10n. This can be done using one or more communication satellites (not shown) and an uplink transmitting station (not shown). Uni-directional communication can include, for example, satellite radio services, wherein programming content (news, music, etc.) is received by the transmitting station, packaged for upload, and then sent to the satellite, which broadcasts the programming to subscribers. Bi-directional communication can include, for example, satellite telephony services using the satellite to relay telephone communications between the autonomous vehicle 10 and the station. The satellite telephony can be utilized either in addition to or in lieu of the wireless carrier system 60.

A land communication system 62 may further be included that is a conventional land-based telecommunications network connected to one or more landline telephones and connects the wireless carrier system 60 to the remote transportation system 52. For example, the land communication system 62 may include a public switched telephone network (PSTN) such as that used to provide hardwired telephony, packet-switched data communications, and the Internet infrastructure. One or more segments of the land communication system 62 can be implemented through the use of a standard wired network, a fiber or other optical network, a cable network, power lines, other wireless networks such as wireless local area networks (WLANs), or networks providing broadband wireless access (BWA), or any combination thereof. Furthermore, the remote transportation system 52 need not be connected via the land communication system 62, but can include wireless telephony equipment so that it can communicate directly with a wireless network, such as the wireless carrier system 60.

Although only one user device 54 is shown in FIG. 2, embodiments of the operating environment 50 can support any number of user devices 54, including multiple user devices 54 owned, operated, or otherwise used by one person. Each user device 54 supported by the operating environment 50 may be implemented using any suitable hardware platform. In this regard, the user device 54 can be realized in any common form factor including, but not limited to: a desktop computer; a mobile computer (e.g., a tablet computer, a laptop computer, or a netbook computer); a smartphone; a video game device; a digital media player; a piece of home entertainment equipment; a digital camera or video camera; a wearable computing device (e.g., smart watch, smart glasses, smart clothing); or the like. Thus, the user device 54 may be a portable device. Each user device 54 supported by the operating environment 50 is realized as a computer-implemented or computer-based device having the hardware, software, firmware, and/or processing logic needed to carry out the various techniques and methodologies described herein. For example, the user device 54 includes a microprocessor in the form of a programmable device that includes one or more instructions stored in an internal memory structure and applied to receive binary input to create binary output. In some embodiments, the user device 54 includes a GPS module capable of receiving GPS satellite signals and generating GPS coordinates based on those signals. In other embodiments, the user device 54 includes cellular communications functionality such that the device carries out voice and/or data communications over the communication network 56 using one or more cellular communications protocols, as are discussed herein. In various embodiments, the user device 54 includes a visual display, such as a touch-screen graphical display, or other display.

Generally, the communication network 56 enables communication between the user device 54 and the autonomous vehicle 10 such that the communication system 36 receives one or more activation requests and/or user preferences from the user device 54, which are communicated to the physiological control system 100. The activation requests and/or user preferences can be provided via a user input device associated with the user device 54 (such as a keyboard, speech recognition system, etc.). In addition, the activation requests and/or user preferences can be provided via an application (i.e. "app") running on the user device 54.

The communication network 56 also enables communication between the physiological monitoring device 102 and the autonomous vehicle 10. Generally, the communication system 36 is in communication with the physiological monitoring device 102 such that the controller 34 receives one or more physiological sensor signals or physiological sensor data, which are communicated to the physiological control system 100. Further, the physiological monitoring device 102 may communicate the one or more physiological sensor signals or physiological sensor data to a remote physiological processing system 66 and/or external authority systems 80 via the communication network 56.

Although only one physiological monitoring device 102 is shown in FIG. 2, embodiments of the operating environment 50 can support any number of physiological monitoring devices 102, including multiple physiological monitoring devices 102 owned, operated, or otherwise used by one person, which may monitor different physiological traits for example. The physiological monitoring device 102 is in communication with the controller 34 to provide physiological sensor data or sensor signals to the physiological control system 100 over the communication network 56. Each physiological monitoring device 102 supported by the operating environment 50 may be implemented using any suitable hardware platform. In addition, each physiological monitoring device 102 supported by the operating environment 50 is realized as a computer-implemented or computer-based device having the hardware, software, firmware, and/or processing logic needed to carry out the various techniques and methodologies described herein. For example, the physiological monitoring device 102 includes a microprocessor in the form of a programmable device that includes one or more instructions stored in an internal memory structure and applied to receive binary input to create binary output.

In various embodiments, the physiological monitoring device 102 includes one or more physiological sensors 104 and a physiological communication system 106. The physiological monitoring device 102 also includes a physiological control module 108. In one example, the physiological sensors 104, the physiological communication system 106 and the physiological control module 108 are contained within a housing 110, which is coupled to the user (i.e. driver, operator or passenger(s)) of the autonomous vehicle 10. Thus, in one example, the physiological monitoring device 102 may comprise a wearable device, which is positionable upon the body of the user and can be coupled to the body of the user, for example, a ring, chest band, bracelet, and other wearable devices, including, but not limited to, portable electronic devices in the form of watches, rings, earrings, bracelets, cufflinks, necklaces, ties, glasses, chest band, smart clothes, etc. Thus, in certain embodiments, physiological monitoring device 102 comprises a personal device associated with the operator of the autonomous vehicle 10, which can be carried with the operator and brought into the autonomous vehicle 10 with the operator upon use of the autonomous vehicle 10. It will be appreciated that the physiological monitoring device 102 may comprise one or more physiological monitoring devices that are fixedly coupled to the autonomous vehicle 10, and thus, not wearable by the user.

The physiological sensors 104 observe one or more physiological traits of the user and generate sensor signals based thereon. In various embodiments, the physiological sensors 104 observe a physiological trait, such as a blood pressure, a pulse rate, a body temperature, a respiration rate, a blood sugar, an alcohol level (e.g. blood alcohol level), and a body movement of the user, and generate sensor signals based thereon. It should be noted that the physiological sensors 104 may observe other traits or characteristics of the user, and that the above list is merely exemplary. The physiological control module 108 receives the sensor signals from the physiological sensors 104 and controls the physiological communication system 106 to transmit the sensor signals from the physiological sensors 104 to the controller 34 associated with the vehicle 10 and/or to the remote physiological processing system 66 via the communication network 56. In various embodiments, the physiological control module 108 also controls the physiological communication system 106 to transmit the sensor signals from the physiological sensors 104 to the user device 54 and/or the external authority systems 80 via the communication network 56.

The sensor signals from the physiological sensors 104 are transmitted by the physiological communication system 106 to the communication system 36, the remote physiological processing system 66, the user device 54 and/or the external authority systems 80 via the communication network 56. The physiological communication system 106 is in communication with the communication system 36, the remote physiological processing system 66, the user device 54 and/or the external authority systems 80 via any suitable communication protocol supported by the operating environment 50, and thus, the physiological communication system 106 can include, but is not limited to, a Bluetooth® transceiver, a radio transceiver, a cellular transceiver, a 2G/3G/4G LTE transceiver and/or a Wi-Fi transceiver. The physiological communication system 106 can also comprise a one-way transmitter. Moreover, the physiological communication system 106 can be in wired communication with the controller 34 to provide input to the physiological control system 100.

The remote transportation system 52 includes one or more backend server systems, which may be cloud-based, network-based, or resident at the particular campus or geographical location serviced by the remote transportation system 52. The remote transportation system 52 can be manned by a live advisor, or an automated advisor, or a combination of both. The remote transportation system 52 can communicate with the user devices 54 and the autonomous vehicles 10*a*, 10*b* . . . 10*n* to schedule rides, dispatch autonomous vehicles 10*a*, 10*b* . . . 10*n*, and the like. In various embodiments, the remote transportation system 52 stores account information such as subscriber authentication information, vehicle identifiers, profile records, behavioral patterns, and other pertinent subscriber information.

In accordance with a typical use case workflow, a registered user of the remote transportation system 52 can create a ride request via the user device 54. The ride request will typically indicate the passenger's desired pickup location (or current GPS location), the desired destination location (which may identify a predefined vehicle stop and/or a user-specified passenger destination), and a pickup time. The remote transportation system 52 receives the ride request, processes the request, and dispatches a selected one of the autonomous vehicles 10*a*-10*n* (when and if one is available) to pick up the passenger at the designated pickup location and at the appropriate time. The remote transportation system 52 can also generate and send a suitably configured confirmation message or notification to the user device 54, to let the passenger know that a vehicle is on the way.

In various embodiments, the remote transportation system 52 includes a remote physiological processing system 66 that is responsive to a remote notification received from the physiological control system 100 of the autonomous vehicle 10 via the communication network 56. Generally, the remote physiological processing system 66 includes a remote physiological control module 68 and a remote communication system 70. The remote communication system 70 is in communication with the communication system 36 associated with the autonomous vehicle 10, and is also in communication with one or more external authority systems 80 over the communication network 56. In various embodiments, the remote communication system 70 comprises a Bluetooth® transceiver, a radio transceiver, a cellular transceiver, a 2G/3G/4G LTE transceiver and/or a Wi-Fi transceiver, and may also be configured to encode data or generate encoded data. The remote communication system 70 transmits data received from the remote physiological control module 68 to the external authority systems 80, and receives the remote notification from the physiological control system 100 of the autonomous vehicle 10.

The remote physiological control module 68 receives the remote notification and based on the remote notification, outputs data to the external authority systems 80. In various embodiments, the remote physiological control module 68 accesses a remote datastore 72, and retrieves a user profile based on the receipt of the remote notification. The remote datastore 72 stores one or more user profiles. In one example, each user profile includes, but is not limited to, health and/or medical records, emergency contact information, residence information, etc. associated with the user of the physiological monitoring device 102. The user profile can be populated by the user via a web-based application, or via the application on the user device 54. The user profile may also be populated based on data gathered from the physiological monitoring device 102, which may also be in communication with the remote physiological processing system 66 to populate the respective user profile in the remote datastore 72. The data output by the remote physiological control module 68 to the external authority systems 80 includes the user profile, a current location of the vehicle 10 and physiological data received from the physiological monitoring device 102.

In various examples, the external authority systems 80 include, but are not limited to, a remote vehicle or user support system, a police dispatch system, an emergency medical response dispatch system, a healthcare provider, an insurance underwriter or insurance company, one or more emergency contacts associated with the user based on the retrieved user profile, a taxi dispatch system and/or a rental car dispatch system. The remote transportation system 52 may also be an external authority system. The external authority systems 80 each include a communication component, such as a wireless communication component, Bluetooth® transceiver, a radio transceiver, a cellular transceiver, a 2G/3G/4G LTE transceiver and/or a Wi-Fi transceiver to receive the data transmitted by the remote communication system 70. The remote communication system 70 may also communicate directly with the external authority systems 80 via email over the internet or a web-based application via the communication network 56. The communication system 36 associated with the vehicle 10 can also output one or more messages (email, text, etc.) to the external authority systems 80, directly via the communication network 56.

As can be appreciated, the subject matter disclosed herein provides certain enhanced features and functionality to what may be considered as a standard or baseline autonomous vehicle 10 and/or an autonomous vehicle based remote transportation system 52. To this end, an autonomous vehicle and autonomous vehicle based remote transportation system can be modified, enhanced, or otherwise supplemented to provide the additional features described in more detail below.

Figure 3:
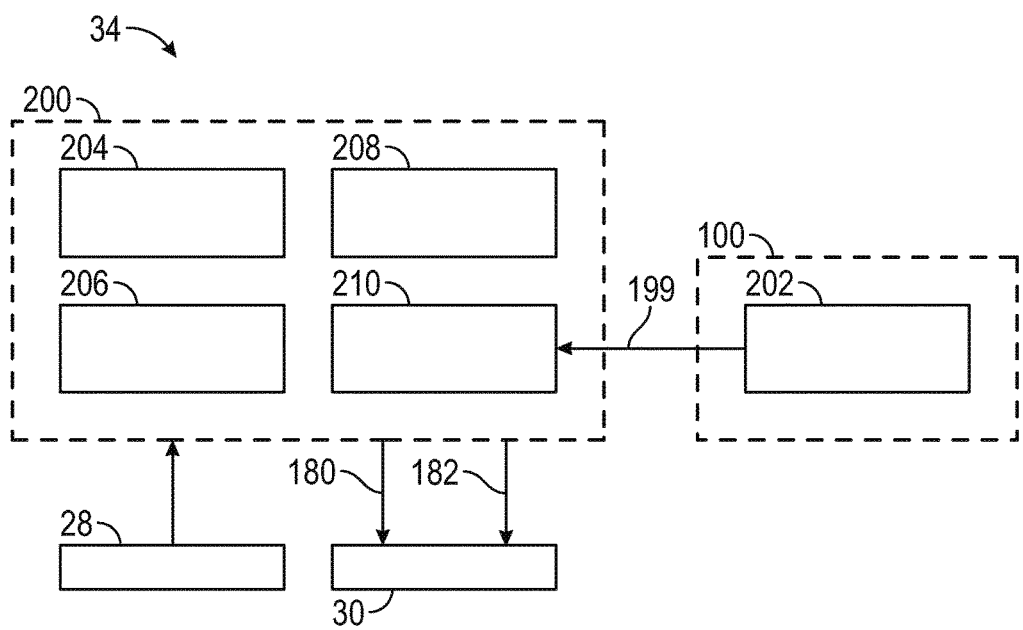
FIG. 3 is a dataflow diagram illustrating an autonomous driving system that includes the physiological control system of the autonomous vehicle, in accordance with various embodiments.

Referring now to FIG. 3, and with continued reference to FIG. 1, in accordance with various embodiments, the controller 34 implements the autonomous driving system (ADS) 200. That is, suitable software and/or hardware components of controller 34 (e.g., processor 44 and computer-readable storage device 46) are utilized to provide an autonomous driving system 200 that is used in conjunction with vehicle 10.

In various embodiments, the instructions of the autonomous driving system 200 may be organized by function or system. For example, as shown in FIG. 3, the autonomous driving system 200 can include a sensor fusion system 124, a positioning system 126, a guidance system 128, and a vehicle control system 130. As can be appreciated, in various embodiments, the instructions may be organized into any number of systems (e.g., combined, further partitioned, etc.) as the disclosure is not limited to the present examples.

In various embodiments, the sensor fusion system 124 synthesizes and processes sensor data and predicts the presence, location, classification, and/or path of objects and features of the environment of the vehicle 10. In various embodiments, the sensor fusion system 124 can incorporate information from multiple sensors, including but not limited to cameras, lidars, radars, and/or any number of other types of sensors.

The positioning system 126 processes sensor data along with other data to determine a position (e.g., a local position relative to a map, an exact position relative to lane of a road, vehicle heading, velocity, etc.) of the vehicle 10 relative to the environment. The guidance system 128 processes sensor data along with other data to determine a path for the vehicle 10 to follow. The vehicle control system 130 generates control signals for controlling the vehicle 10 according to the determined path. In various embodiments, the guidance system 128 also processes the exact position of the vehicle 10 and the map data from the data storage device 32 to determine one or more geographical locations for receiving treatment, resting and/or stopping the vehicle 10, including, but not limited to, one or more nearby hotels, hospitals, urgent cares, clinics, parking lots, gas stations, drug stores, etc.

In various embodiments, the controller 34 implements machine learning techniques to assist the functionality of the controller 34, such as feature detection/classification, obstruction mitigation, route traversal, mapping, sensor integration, ground-truth determination, and the like.

In various embodiments, the vehicle control system 130 receives an output 199 from a physiological control module 202 of the physiological control system 100. The vehicle control system 130 controls the operation of the vehicle 10 based thereon. In one example, the vehicle control system 130 receives the output 199 from the physiological control system 100 and generates at least one of a vehicle control output 180 and a second vehicle control output 182. The vehicle control output 180 includes a set of actuator commands to control the operation of the vehicle 10 along a determined path, including, but not limited to, a steering command, a shift command, a throttle command, and a brake command. The second vehicle control output 182 includes a set of actuator commands to achieve a commanded setting for comfort or convenience from the vehicle control system 130, including, but not limited to, a HVAC command, a seat command, an infotainment command, a lock command, a lighting command, a window command and an alarm command.

The vehicle control output 180 and the second vehicle control output 182 are communicated to the actuator system 30. In an exemplary embodiment, the actuators 42 include a steering control, a shifter control, a throttle control, a brake control, a HVAC control, a seat control, an infotainment control, a lock control, a lighting control, a window control and an alarm control. The steering control may, for example, control a steering system 24 as illustrated in FIG. 1. The shifter control may, for example, control a transmission system 22 as illustrated in FIG. 1. The throttle control may, for example, control a propulsion system 20 as illustrated in FIG. 1. The brake control may, for example, control wheel brake system 26 as illustrated in FIG. 1. The HVAC control may, for example, control the HVAC system 21 as illustrated in FIG. 1. The seat control may, for example, control seat system 23 as illustrated in FIG. 1. The infotainment control may, for example, control the infotainment system 25 as illustrated in FIG. 1. The lock control may, for example, control lock system 27 as illustrated in FIG. 1. The lighting control may, for example, control the lighting system 29 as illustrated in FIG. 1. The window control may, for example, control the window system 31 as illustrated in FIG. 1. The alarm control may, for example, control the alarm system 33 as illustrated in FIG. 1.

As mentioned briefly above, the physiological control system 100 of FIG. 1 is included within the autonomous driving system 200, for example, for generating the vehicle control output 180 and second vehicle control output 182 by the vehicle control system 130. As will be discussed, the physiological control system 100 generates the output 199, which is used by the vehicle control system 130 to generate the vehicle control output 180 and/or second vehicle control output 182 that is communicated to the actuator system 30. Thus, the physiological control system 100 generates the output 199 that is used by the vehicle control system 130 to control one or more of the actuators 42 of the actuator system 30 based on the systems and methods of the present disclosure.

Figure 4:
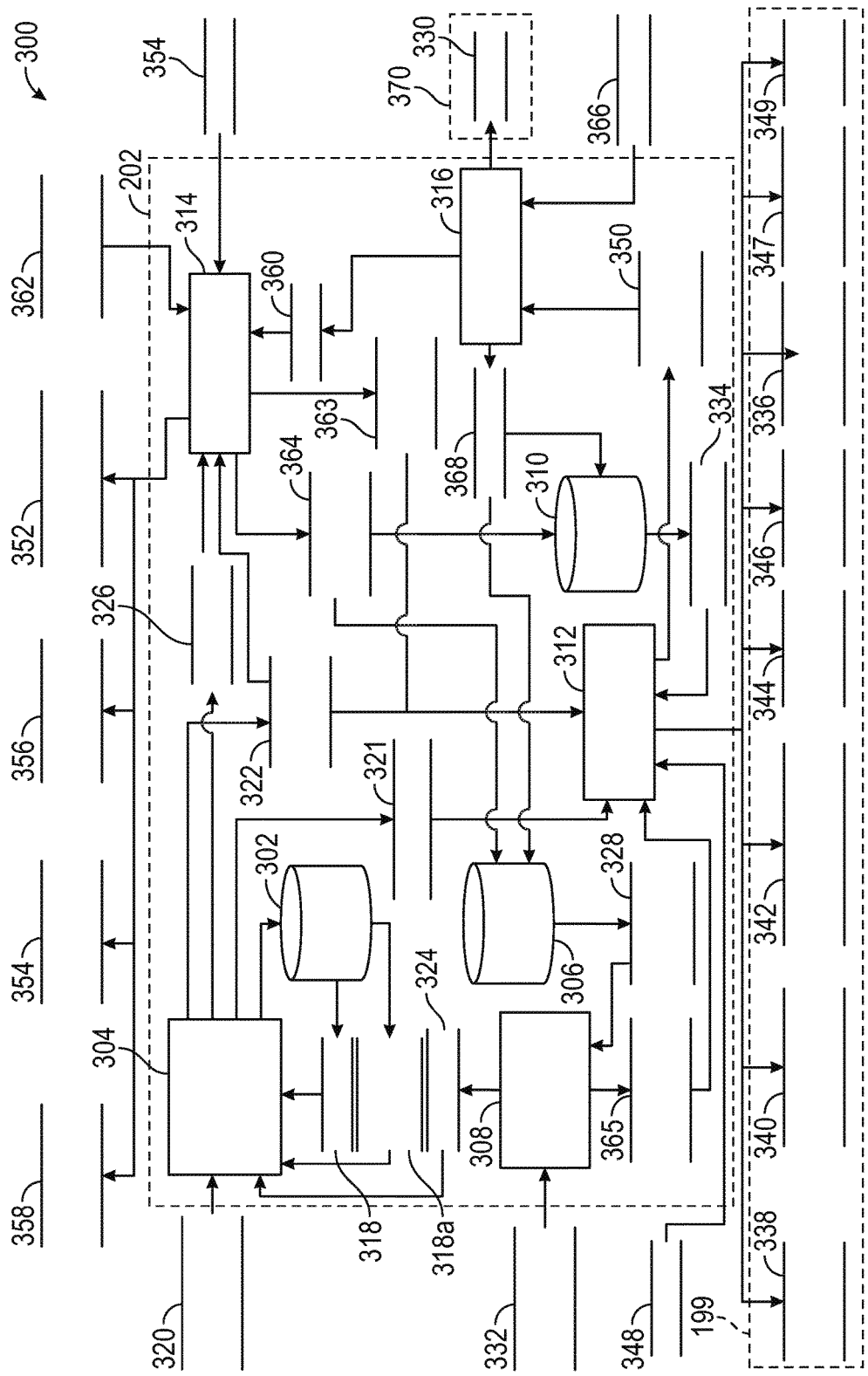
FIG. 4 is a dataflow diagram illustrating a control system of the physiological control system of the autonomous vehicle of FIG. 1 in accordance with various embodiments.

For example, as shown in more detail with regard to FIG. 4 and with continued reference to FIG. 3, the physiological control system 100 includes the physiological control module 202. In various embodiments, the physiological control module 202 outputs the output 199 to the vehicle control system 130 based on the sensor signals from the physiological monitoring device 102, the sensor signals from the response sensors 39, inputs from the user device 54, inputs from the input device 25b and based on the vehicle control systems and methods of the present disclosure. The physiological control module 202 outputs a remote notification, physiological data and a location of the vehicle 10 for the remote physiological processing system 66 based on the sensor signals from the physiological monitoring device 102, the sensor signals from the response sensors 39, inputs from the user device 54, inputs from the input device 25b and based on the vehicle control systems and methods of the present disclosure. In various embodiments, the physiological control module 202 also outputs a message for one or more of the external authority systems 80 based on the sensor signals from the physiological monitoring device 102, the sensor signals from the response sensors 39, inputs from the user device 54, inputs from the input device 25b and based on the vehicle control systems and methods of the present disclosure. The physiological control module 202 also outputs an interface for display on the display 25a based on the sensor signals from the physiological monitoring device 102 and based on the vehicle control systems and methods of the present disclosure.

Referring now to FIG. 4, and with continued reference to FIGS. 1-3, a dataflow diagram illustrates various embodiments of a control system 300 for the physiological control system 100, which may be embedded within the physiological control module 202. Various embodiments of the control system 300 according to the present disclosure can include any number of sub-modules embedded within the physiological control module 202. As can be appreciated, the sub-modules shown in FIG. 4 can be combined and/or further partitioned to similarly generate the output 199 for the vehicle control system 130, to transmit data to the remote physiological processing system 66 and/or the external authority systems 80 and to output the interface for display on the display 25a. Inputs to the control system 300 may be received from the physiological monitoring device 102 (FIG. 1), received from the input device 25b of the infotainment system 25 (FIG. 1), received from the user device 54 (FIG. 1), received from the response sensors 39 associated with the vehicle 10, received from other control modules (not shown) associated with the vehicle 10, and/or determined/modeled by other sub-modules (not shown) within the physiological control module 202. In various embodiments, the physiological control module 202 includes a values datastore 302, a physiological monitor module 304, a response datastore 306, a response recognition module 308, a setting datastore 310, a conditions control module 312, a communication control module 314 and a user interface (UI) control module 316.

The values datastore 302 stores one or more tables (e.g., lookup tables) that indicate one or more acceptable values for one or more physiological traits, and also stores a baseline physiological reading. In other words, the values datastore 302 stores one or more tables that provide one or more predefined acceptable values 318 for the physiological traits observed and measured by the physiological sensors 104, and also stores an initial or baseline reading 318a from the physiological sensors 104. In various embodiments, the tables may be interpolation tables that are defined by one or more indexes. One or more values 318 provided by at least one of the tables generally indicates a normal or acceptable range for the respective physiological traits. For example, one or more values 318 comprise an acceptable range for a blood pressure, an acceptable range for a pulse rate, an acceptable range for a body temperature, an acceptable range for a respiration rate, an acceptable range for blood sugar, an acceptable range for a blood alcohol level, an acceptable range for an amount of movement. As an example, one or more tables can be indexed by various parameters such as, but not limited to, blood pressure, pulse rate, body temperature, respiration rate, blood sugar, blood alcohol level or movement, to provide the one or more values 318. The baseline reading 318a comprises a blood pressure, a pulse rate, a body temperature, a respiration rate, a blood sugar and/or a blood alcohol level initially observed and measured by the physiological sensors 104, which is stored in the values datastore 302 by the physiological monitor module 304.

The physiological monitor module 304 receives as input physiological sensor data 320. The physiological sensor data 320 comprises the sensor signals from the physiological sensors 104 associated with the physiological monitoring device 102. The physiological monitor module 304 processes the physiological sensor data 320 and generates the baseline physiological reading 318a based on an initial receipt of the physiological sensor data 320 (such as upon a start-up of the vehicle 10). The physiological monitor module 304 stores the baseline physiological reading 318a in the values datastore 302. Based on a sampling rate associated with the physiological sensors 104, upon the receipt of later sampled physiological sensor data 320 (i.e. physiological sensor data 320 received after the initial baseline reading), the physiological monitor module 304 compares the subsequent physiological sensor data 320 to the baseline physiological reading 318a and determines whether one or more physiological traits have changed. Based on this determination, the physiological monitor module 304 sets a physiological change 321 for the conditions control module 312. Exemplary physiological changes include, but are not limited to, an increase/decrease in blood pressure, an increase/decrease in pulse rate, an increase/decrease in body temperature, an increase/decrease in respiration rate, an increase/decrease in blood sugar, an increase/decrease in movement, etc.

The physiological monitor module 304 also processes the physiological sensor data 320, and retrieves the one or more values 318 from the values datastore 302. Based on the retrieved one or more values 318, the physiological monitor module 304 determines whether the physiological sensor data 320 is within an acceptable range. If the physiological sensor data 320 is outside of the acceptable range, the physiological monitor module 304 sets a physiological condition 322 for the communication control module 314 and the UI control module 316. The physiological condition 322 indicates that the physiological sensor data 320 is abnormal or outside of the acceptable one or more values 318.

The physiological monitor module 304 also receives as input a response 324 from the response recognition module 308. The response 324 is a response from the user to dismiss a prompt 330 output by the UI control module 316 based on the receipt of the physiological condition 322. Based on the response 324, the physiological monitor module 304 sets the physiological data 326, which can include the determined physiological condition and the received physiological sensor data 320, for the communication control module 314.

The response datastore 306 stores one or more response settings 328. In other words, the response datastore 306 stores one or more settings for responses by the vehicle 10 to gestures made by the user. For example, the response datastore 306 stores one or more response settings 328 that correspond with a user made gesture for responding to the prompt 330 from the UI control module 316. In other words, the response datastore 306 stores one or more predefined vehicle responses (response settings) for a particular gesture made by the user. In various embodiments, the response settings 328 are user configured by inputs received from the user device 54 and/or from inputs received from the input device 28b, as discussed further herein. In other embodiments, the response settings are default or factory settings. In various embodiments, the response datastore 306 stores the response setting 328 that associates a particular user gesture with an dismissal of the prompt 330, and stores the response setting 328 that associates a particular user gesture with an activation command for the conditions control module 312.

The response recognition module 308 receives as input response sensor data 332. The response sensor data 332 comprises the sensor signals from the response sensors 39. The response recognition module 308 processes the response sensor data 332 and accesses the response datastore 306 to retrieve the response setting 328 that corresponds with the gesture observed by the response sensors 39. Based on the response setting 328, the response recognition module 308 determines the desired vehicle response based on the gesture observed by the response sensors 39. In various embodiments, based on the response setting 328, the response recognition module 308 sets the response 324 for the physiological monitor module 304 that indicates the dismissal of the prompt 330 by the user via an observed gesture. Based on the response setting 328, the response recognition module 308 also sets a gesture activation 365 for the conditions control module 312. The gesture activation 365 indicates receipt of a gesture from the user to activate the conditions control module 312.

The setting datastore 310 stores one or more settings associated with the control of the systems of the vehicle 10, including, but not limited to the vehicle control system 130, the HVAC system 21, the seat system 23, the infotainment system 25, the lock system 27, the lighting system 29, the window system 31 and the alarm system 33, based on the determined physiological change 321 and the determined physiological condition 322. In various embodiments, the setting datastore 310 stores one or more tables (e.g., lookup tables) that indicate a predefined control command for one or more of the HVAC system 21, the seat system 23, the infotainment system 25, the lock system 27, the lighting system 29, the window system 31 and the alarm system 33 based on the physiological change 321 and the physiological condition 322. In other words, the setting datastore 310 stores one or more tables that provide one or more settings 334 associated with the determined physiological change 321, and provide one or more settings 334 based on the determined physiological condition 322. In various embodiments, the tables are user defined based on inputs received from the user device 54 and/or inputs received from the input device 28b. In other embodiments, the tables are predefined based on default values and based on user defined preferences. As an example, one or more tables can be indexed by various parameters such as, but not limited to, the particular system of the vehicle 10, the physiological change 321 or the physiological condition 322, to provide the one or more settings 334.

The conditions control module 312 receives as input the physiological change 321 and the physiological condition 322. The conditions control module 312 processes the physiological change 321 and the physiological condition 322; and retrieves the corresponding settings 334. The conditions control module 312 outputs the output 199 for the vehicle control system 130, which includes HVAC data 336, seat data 338, vehicle controls data 340, infotainment data 342, light data 344, lock data 346, window control data 347 and alarm data 349 based on the retrieved settings 334. In one example, the HVAC data 336 comprises one or more control signals for the vehicle control system 130 to command the actuator system 30 to control the HVAC system 21 to increase or decrease a temperature of a cabin of the vehicle 10 (for example, one or more control signals to the motor, the condenser and/or the heater). The seat data 338 comprises one or more control signals for the vehicle control system 130 to command the actuator system 30 to control the seat system 23 to activate a seat cooler, a seat warmer and/or one or more of the actuators associated with a respective seat to move the seat. The vehicle controls data 340 comprises one or more control signals for the vehicle control system 130 to autonomously or semi-autonomously control the operation of the vehicle 10 via one or more commands to the actuator system 30 to control the steering system 24, the transmission system 22, the propulsion system 20 and/or the wheel brake system 26. The vehicle controls data 340 may also include one or more control signals for the vehicle control system 130 to command the actuator system 30 control the wheel brake system 26 and/or propulsion system 20 to limit a speed of the vehicle 10.

The infotainment data 342 comprises one or more control signals for the vehicle control system 130 to command the actuator system 30 to command the infotainment system 25 to change a music station, play a predefined playlist, recommend an entertainment or activity, etc. The light data 344 comprises one or more control signals for the vehicle control system 130 to command the actuator system 30 to command the lighting system 29 to illuminate a light source of the vehicle 10, including, but not limited to, turning on/off one or more interior lights, turning on/off one or more exterior lights, changing a color associated with one or more interior lights, etc. The lock data 346 comprises one or more control signals for the vehicle control system 130 to command the actuator system 30 to command the lock system 27 to lock or unlock one or more locks associated with one or more doors and/or cargo access panels associated with the vehicle 10, including, but not limited to, unlocking or locking one of the doors/cargo access panels, unlocking/locking all of the doors/cargo access panels, etc. The window control data 347 comprises one or more control signals for the vehicle control system 130 to command the actuator system 30 to command the window system 31 to move one or more of the windows associated with the vehicle 10, including, but not limited to, open and/or close one window, open and/or close all windows, open and/or close a driver's side window, open and/or close a passenger window, and open and/or close a sunroof and/or convertible roof of the vehicle 10. The alarm data 349 comprises one or more control signals for the vehicle control system 130 to command the actuator system 30 to command the alarm system 33 to activate or deactivate the alarm.

The conditions control module 312 also receives as input navigation data 348. The navigation data 348 comprises information regarding locations available for receiving treatment, resting and/or stopping the vehicle 10 based on a current geographic location of the vehicle 10, which is received from the autonomous driving system 200, such as the guidance system 128. The navigation data 348 may also be received directly from the remote transportation system 52. The conditions control module 312 processes the navigation data 348, and based on the navigation data 348 and the physiological condition 322, the conditions control module 312 sets location options 350 for the UI control module 316. The location options 350 comprise one or more nearby locations for receiving treatment, resting and/or stopping the vehicle 10, including, but not limited to, one or more nearby hotels, hospitals, urgent cares, clinics, parking lots, gas stations, drug stores, etc. A nearest location for treatment may also be output to the vehicle control system 130 to autonomously or semi-autonomously control the operation of the vehicle 10 to that location for treatment.

The communication control module 314 receives as input the physiological data 326 and the physiological condition 322 from the physiological monitor module 304. The communication control module 314 processes the physiological data 326 and the physiological condition 322; and outputs physiological condition data 352 for transmission by the communication system 36 to the remote physiological processing system 66. The physiological condition data 352 comprises the physiological data 326 and the physiological condition 322 received from the physiological monitor module 304, and may include an identifier of the user of the physiological monitoring device 102. The communication control module 314 also outputs GPS data 354 and a remote notification 356 for transmission by the communication system 36 to the remote physiological processing system 66. The GPS data 354 comprises the current geographical location of the vehicle 10 as received from autonomous driving system 200, such as the positioning system 126, and the remote notification 356 comprises a notification that the physiological sensor data 320 is outside of the acceptable range, as indicated by the physiological condition 322.

Based on the physiological data 326 and the physiological condition 322, the communication control module 314 also outputs a message 358. In various embodiments, the message 358 is output for the communication system 36 for transmission to the external authority systems 80. For example, the message 358 comprises an email or text message to a user device associated with a contact 360, such as an emergency contact, received from the UI control module 316. The emergency contact may also be received as input from the user device 54 associated with the vehicle 10.

The communication control module 314 also receives as input portable device data 362 from the user device 54. The portable device data 362 comprises inputs received to the user device 54, which include, but are not limited to, preferences for vehicle responses to user gestures, such as gestures for responding to prompts, preferences for one or more settings associated with one or more physiological conditions, and one or more emergency contacts. The communication control module 314 processes the portable device data 362 and sets device preferences 364 for the response datastore 306 and the setting datastore 310. The communication control module 314 also processes the portable device data 362 for the one or more contacts, and in various embodiments, the communication control module 314 transmits the message 358 to the one or more contacts identified in the portable device data 362. In various embodiments, the communication control module 314 also processes the portable device data 362 and determines whether an activation request has been received to output the output 199 to the vehicle control system 130. If the activation request is received, the communication control module 314 may set activation data 363 for the conditions control module 312. Based on the receipt of the activation data 363, the conditions control module 312 outputs the output 199, which includes one or more of the HVAC data 336, seat data 338, vehicle controls data 340, infotainment data 342, light data 344 and lock data 346 based on the determined physiological change 321 and/or the physiological condition 322.

In various embodiments, one or more of the communication control module 314 and the conditions control module 312 can be enabled based on one or more sensor signals received from the response sensors 39. Stated another way, the response recognition module 308 may process the response sensor data 332 by retrieving the response setting 328 associated with the identified gesture, and determine that the vehicle response is the gesture activation 365. Based on this determination, the response recognition module 308 sets the gesture activation 365 for one or more of the communication control module 314 and the conditions control module 312. Based on the gesture activation 365, the communication control module 314 may receive and process the portable device data 362. Based on the gesture activation 365, the conditions control module 312 may receive and process the physiological condition 322 and the physiological change 321. Thus, in various embodiments, a motion or gesture of a user observed by the response sensors 39 may provide an activation request for the conditions control module 312 and/or communication control module 314.

The UI control module 316 receives input data 366. The input data 366 comprises input received to the input device 28b. The UI control module 316 processes the input data 366, and sets preferences 368 for the response datastore 306 and the setting datastore 310; and sets the contact 360 for the communication control module 314. The preferences 368 comprise one or more user defined preferences for gestures in response to the prompt 330 (response setting 328), one or more user defined preferences for gestures to activate the conditions control module 312 (response setting 328) and one or more user defined preferences for settings 334 associated with the one or more physiological conditions or physiological changes. The input data 366 may also comprise an input received to the input device 28b in response to the prompt 330.

The UI control module 316 also receives as input the physiological condition 322 and the location options 350. The UI control module 316 processes the physiological condition 322, and based on the physiological condition 322, the UI control module 316 outputs the prompt 330. The prompt 330 may be part of a user interface 370. The prompt 330 comprises a request for a gesture, a request for physical movement, a graphical, textual and/or voice prompt to the user, which can warn of the determined physiological condition 322, and optionally, provides suggestions for action in view of the determined physiological condition 322. For example, the prompt 330 can include a prompt to place the vehicle 10 in an autonomous drive mode (such that the vehicle 10 operates autonomously) or in a semi-autonomous drive mode. Further, the prompt can include a prompt to suggest a diversion from a planned route to rest or seek treatment. In certain examples, the prompt 330 also includes one or more locations for the user to rest, seek treatment or stop the vehicle 10 based on the location options 350 received from the conditions control module 312.

Figure 5:
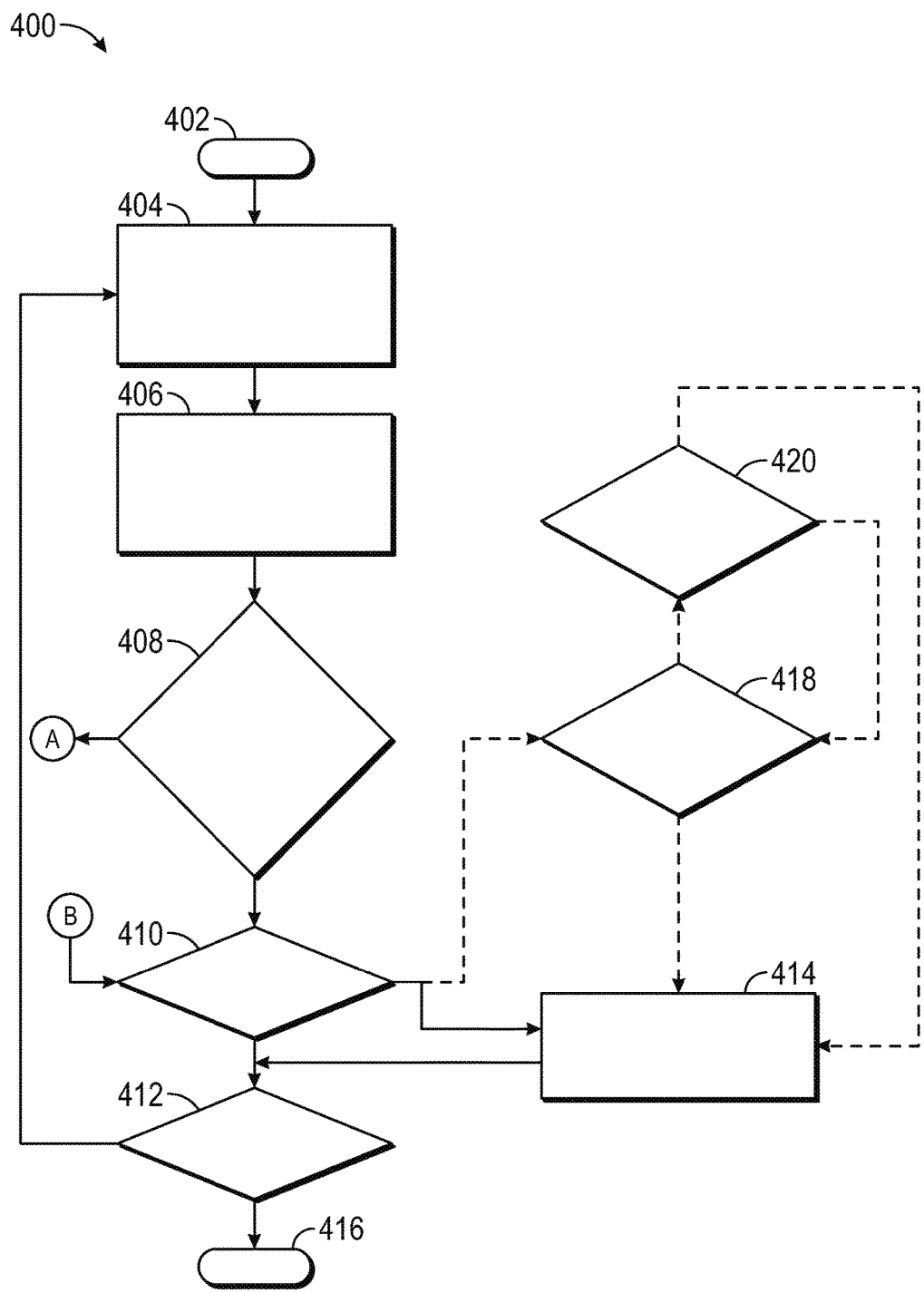
FIG. 5 is a flowchart illustrating a control method of the physiological control system of FIG. 1 in accordance with various embodiments.

Referring now to FIG. 5, and with continued reference to FIGS. 1-2, a flowchart illustrates a control method 400 that can be performed by the physiological control module 202 of FIGS. 1-4 in accordance with the present disclosure. As can be appreciated in light of the disclosure, the order of operation within the method is not limited to the sequential execution as illustrated in FIG. 5, but may be performed in one or more varying orders as applicable and in accordance with the present disclosure.

In various embodiments, the method can be scheduled to run based on predetermined events, based on the receipt of physiological sensor data 320 and/or can run continuously during operation of the autonomous vehicle 10. The method begins at 402. At 404, the method receives the physiological sensor data 320 from the physiological monitoring device 102, and establishes a baseline physiological reading. The baseline physiological reading is generally taken upon initiation of the physiological control system 100, and provides initial sensor signals or sensor data received from the physiological monitoring device 102. The method stores this baseline physiological reading 318a in the values datastore 302. At 406, the method processes the physiological sensor data 320 to determine the physiological change 321 and the physiological condition 322, and retrieves the one or more values 318. At 408, the method determines whether the received physiological sensor data 320 is outside of the acceptable values 318. If the physiological sensor data 320 is outside of the one or more acceptable ranges based on the one or more values 318, the method goes to A on FIG. 6.

Otherwise, at 410, the method determines whether the received physiological sensor data 320 has changed from the baseline physiological reading. If the physiological sensor data 320 has not changed from the baseline physiological reading 318a, or if the physiological sensor data 320 is within a predefined tolerance for variances from the baseline physiological reading 318a, the method proceeds to 412. Otherwise, the method determines the physiological change 321 and proceeds to 414. At 412, the method determines whether the vehicle 10 is in operation, which can be based on data received from the sensor system 28. If the vehicle 10 is in operation, the method loops to 404. Otherwise, the method ends at 416.

At 414, the method retrieves the setting 344 based on the determined physiological change 321 and outputs the output 199, which includes one or more control signals for the actuator system 30 to control one or more systems of the vehicle 10, such as the vehicle control system 130, the HVAC system 21, the seat system 23, the infotainment system 25, the lock system 27, the lighting system 29, the window system 31 and the alarm system 33, based on the setting 334 associated with the determined physiological change 321. In various embodiments, the method outputs the output 199 based on the setting 334 associated with the determined physiological change 321.

Optionally, the method proceeds to 418, and determines whether the activation data 363 has been received from the user device 54. If true, the method proceeds to 414, and outputs the output 199, which includes one or more of the HVAC data 336, seat data 338, vehicle controls data 340, infotainment data 342, light data 344, lock data 346, window control data 347 and alarm data 349 based on the activation request received from the user device 54 and the determined physiological change 321. Otherwise, the method proceeds to 420, and determines, based on the sensor signals or sensor data from the response sensors 39, whether the gesture activation 365 has been received. If true, the method proceeds to 414 and outputs the output 199, which includes one or more of the HVAC data 336, seat data 338, vehicle controls data 340, infotainment data 342, light data 344, lock data 346, window control data 347 and alarm data 349 based on the activation request received from the user device 54 and the determined physiological change 321. Otherwise, the method loops to 418. From 414, the method proceeds to 412.

Figure 6:
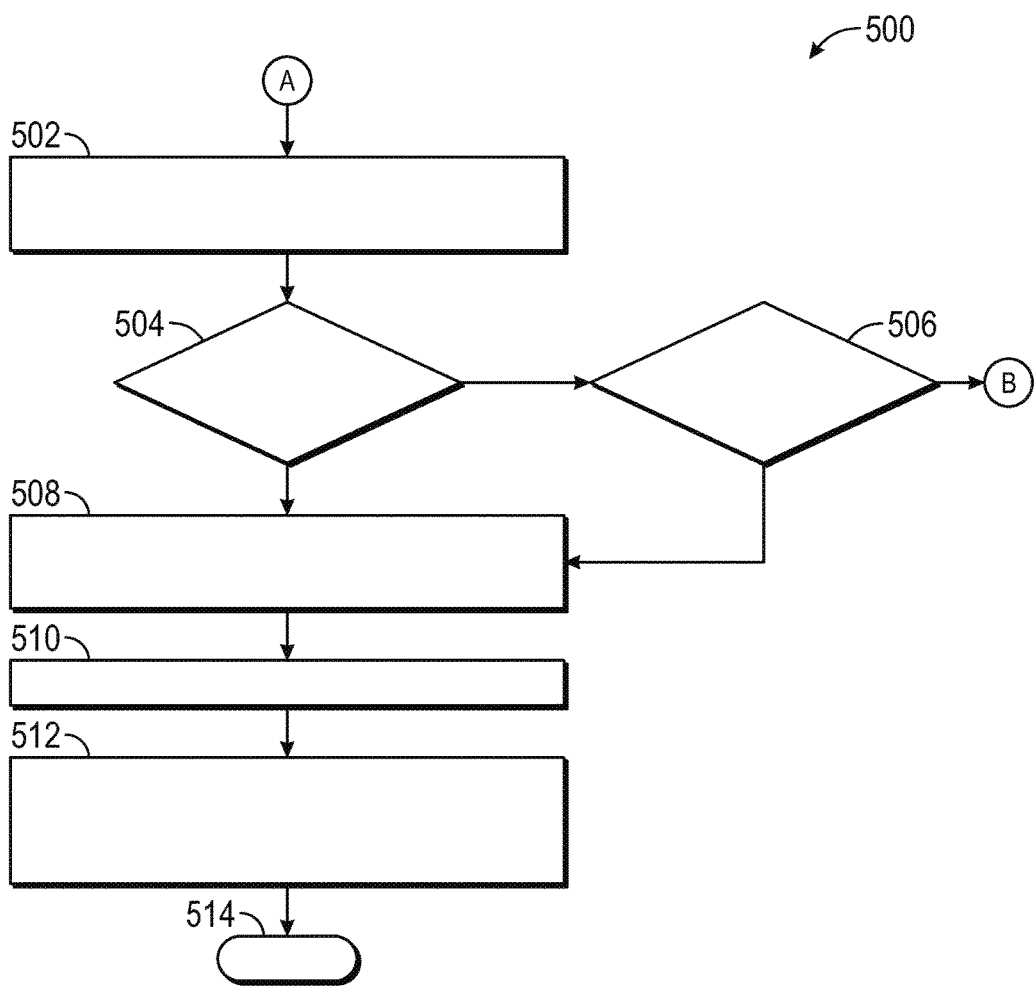
FIG. 6 is a flowchart illustrating a control method of the physiological control system of FIG. 1 in accordance with various embodiments.

With reference to FIG. 6, and with continued reference to FIGS. 1-4, a flowchart illustrates a control method 500 that can be performed by the physiological control module 202 of FIGS. 1-3 in accordance with the present disclosure. As can be appreciated in light of the disclosure, the order of operation within the method is not limited to the sequential execution as illustrated in FIG. 6, but may be performed in one or more varying orders as applicable and in accordance with the present disclosure.

In one example, the method begins at A. At 502, the method outputs the prompt 330 based on the physiological condition 322. At 504, the method determines whether a user response or gesture has been observed based on the sensor signals from the response sensors 39. If a user response or gesture is observed, at 506, the method retrieves the response setting 328 from the response datastore 306 and determines whether the gesture is to dismiss the prompt 330. If the gesture is the dismissal of the prompt 330, the method proceeds to B on FIG. 5.

Otherwise, at 508, the method retrieves the setting 344 based on the determined physiological condition 322 and outputs the output 199 to the vehicle control system 130, which includes the vehicle controls data 340. Optionally, the method outputs the output 199 to the vehicle control system 130 based on the activation request received from the user device 54. At 510, the method outputs the message 358 to the external authority systems 80. At 512, the method outputs the remote notification 356, the physiological condition data 352 and the GPS data 354 to the remote physiological processing system 66. The method ends at 514.

Figure 7:
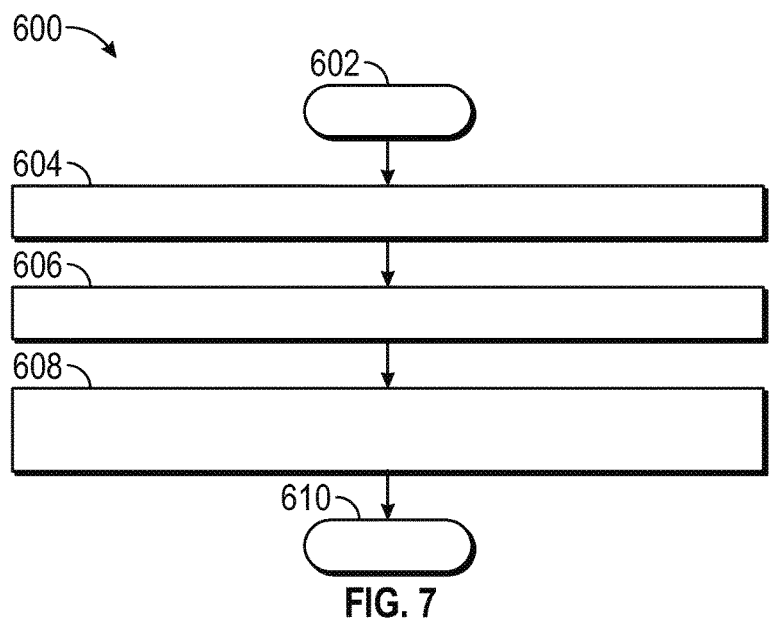
FIG. 7 is a flowchart illustrating a control method of the physiological control system of FIG. 1 in accordance with various embodiments.

With reference to FIG. 7, and with continued reference to FIGS. 1-4, a flowchart illustrates a control method 600 that can be performed by the remote physiological control module 68 of FIGS. 1 and 2 in accordance with the present disclosure. As can be appreciated in light of the disclosure, the order of operation within the method is not limited to the sequential execution as illustrated in FIG. 7, but may be performed in one or more varying orders as applicable and in accordance with the present disclosure.

The method begins at 602. At 604, the method receives the remote notification 356, the GPS data 354 and the physiological condition data 352 from the vehicle 10. At 606, the method processes the received data and retrieves the user profile from the remote datastore 72 based on the data received from the vehicle 10. At 608, the method outputs and transmits the GPS data 354, the user profile and the physiological condition data 352 to the one or more external authority systems 80. The method ends at 610.

It should be noted that the systems (e.g. the HVAC system 21, the seat system 23, the infotainment system 25, the lock system 27, the lighting system 29, the window system 31 and the alarm system 33) and the vehicle control system 130 need not be activated solely on physiological input. Rather, one or more of the systems and/or the vehicle control system 130 can be activated such that one or more control signals are output to the systems (e.g. the HVAC system 21, the seat system 23, the infotainment system 25, the lock system 27, the lighting system 29, the window system 31 and the alarm system 33) and/or the vehicle control system 130 based on receipt of input from the user device 54, vehicle to vehicle communications (V2V), etc.

Gesture-Based Vehicle-User Interaction

Figure 8:
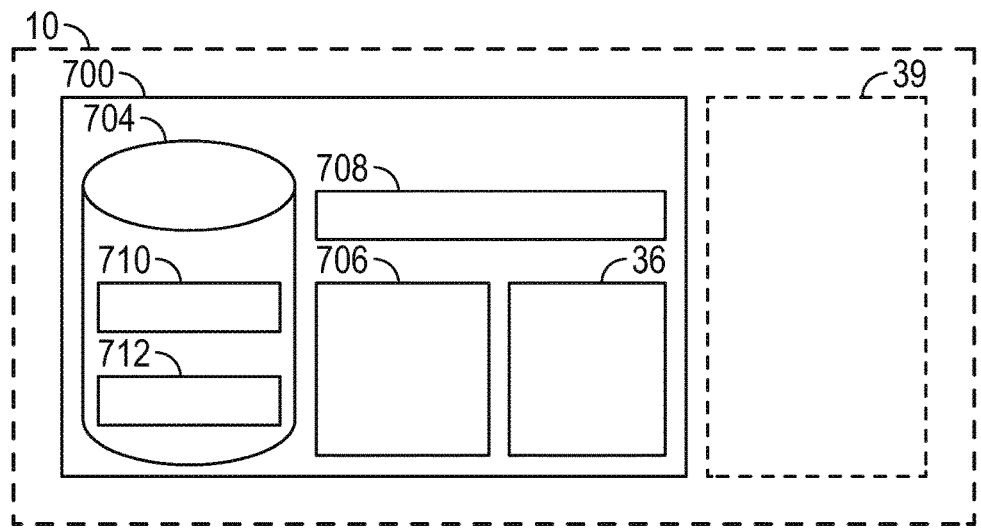
FIG. 8 illustrates schematically an exemplary computer architecture, in accordance with various embodiments.

With reference to FIG. 8, the interaction with the user with the vehicle 10 via one or more gestures is further described. Generally, the vehicle 10 may also be in communication with a wearable device worn by the user that is capable of activating one or more functions of the vehicle based on a bodily gesture. In various embodiments, the wearable device is the physiological monitoring device 102, worn by the user, which communicates with the vehicle 10 to initiate vehicle functions and also communicates sensor signals or sensor data from the one or more physiological sensors 104. Thus, in various embodiments, the physiological monitoring device 102 is configured to send various signals to the vehicle based on user motions involving the physiological monitoring device 102.

The response sensors 39 of the vehicle 10 may include any of select sensors and communication receivers for receiving user inputs, specially programmed computing components for determining vehicle functions corresponding to user inputs, and output components for activating or actuating the vehicle functions identified. Wearable devices, such as the physiological monitoring device 102, are configured in various embodiments to generate and send signals, for receipt by the vehicle 10, based on motion of the user. For example, if a user initiates an emergency call or text message by way of gesture—whether by way moving a worn device, or simply by body movement, the vehicle 10 uses the communication system 36 to make the call or send the text message.

FIG. 8 illustrates the computer-based system 700. In a contemplated embodiment, some or all of the computing system 700 is positioned at a remote call or control center, like the remote transportation system 52 (FIG. 2).

The computer-based system 700 of FIG. 8 can also be a model for other electronic systems of the present technology, such as of a wearable device—e.g., smart bracelet, ring, cufflink(s), belt attachment, shoe or boot (footwear) attachment, legwear, arm wear, clothing, headphones, headgear, hat or other headwear, watch, eyeglasses, sunglasses, earrings, etc.—as described more below, including in connection with FIG. 10. The computer-based system 700 is part of a primary computing unit of the vehicle 10, such as the controller 34 of the vehicle 10 (FIG. 1). The system and components thereof can be hardware-based. The computer-based system 700 includes a computer-readable storage medium, or data storage device 704 and also includes a processing hardware unit 706 connected or connectable to the computer-readable storage device 704 by way of a communication link 708, such as a computer bus. In various embodiments, the processing hardware unit 706 is the processor 44.

The processing hardware unit 706 can include or be multiple processors, which could include distributed processors or parallel processors in a single machine or multiple machines. The processing hardware unit can be used in supporting a virtual processing environment. The processing hardware unit could include a state machine, application specific integrated circuit (ASIC), programmable gate array (PGA) including a Field PGA, or state machine. References herein to the processing hardware unit executing code or instructions to perform operations, acts, tasks, functions, steps, or the like, could include the processing hardware unit performing the operations directly and/or facilitating, directing, or cooperating with another device or component to perform the operations.

In various embodiments, the data storage device 704 is any of a volatile medium, a non-volatile medium, a removable medium, and a non-removable medium. The term computer-readable media and variants thereof, as used in the specification and claims, refer to tangible storage media. The media can be a device, and can be non-transitory. In some embodiments, the storage media includes volatile and/or non-volatile, removable, and/or non-removable media, such as, for example, random access memory (RAM), read-only memory (ROM), electrically erasable programmable read-only memory (EEPROM), solid state memory or other memory technology, CD ROM, DVD, BLU-RAY, or other optical disk storage, magnetic tape, magnetic disk storage or other magnetic storage devices. The data storage device 704 includes one or more storage modules storing computer-readable instructions executable by the processing hardware unit 706 to perform the functions of the computer-based system 700 described herein. For instance, the data storage device 704 includes team-based vehicle-machine framework modules 710.

In various embodiments, the response sensors 39 provide information to the computer-based system 700, including information indicating presence and movement of a proximate vehicle user and a movement of the user within the vehicle 10. In addition, the response sensors 39 may be part of the sensor system 28.

Figure 9:
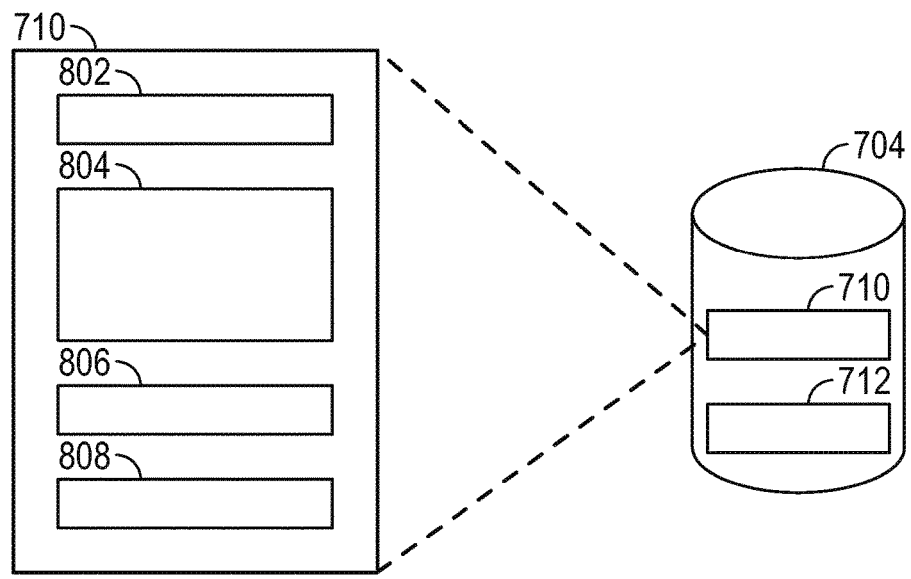
FIG. 9 illustrates example memory components of the computer architecture of FIG. 8 in accordance with various embodiments.

FIG. 9 shows in more detail the data storage device 704 of FIG. 8. The components of the data storage device 704 are now described further with reference to the figure. As provided, the data storage device 704 includes one or more modules 710. And the memory may also include ancillary components 712, such as additional software and/or data supporting performance of the methods of the present disclosure.

The ancillary components 712 can include, for example, one or more user profiles. The profiles can including settings, default and/or custom set, for one or more users (e.g., drivers) of the vehicle. These and other data components are described elsewhere, herein, including below in connection with the methods 1000, of operation. The technology can be personalized, or customized in these ways. In various embodiments, the ancillary components 712 include the response datastore 306.

The modules 710 can include at least three (3) modules 802, 804, 806, described further in the next section. In one embodiment, the modules 710 include one or more additional modules. Some instructions can be part of more than one module, and functions described herein can be performed by processor execution of the corresponding more than one module.

Functions described herein, but not in connection expressly with one of the three modules 802, 804, 806 can be a part of one of the three modules and/or a part of an additional supporting module or modules 808. The supporting module(s) 808 can include, for example, a user-identification module, a passenger-identification module, a learning module (to, e.g., learn user gesture style, or natural movement or gesture types of the user, for improving efficiency and effectiveness or user-system interaction), and/or a recommendation, suggestion or teaching module (e.g., to provide advice to a user on how to gesture for triggering select vehicle functions, for improving efficiency and effectiveness or user-system interaction).

Each of the modules can be referred to by any of a variety of names, such as by a term or phrase indicative of its function. The modules 802, 804, 806 of the computer-based system 700 can be referred to as: a user-gesture determination module 802; a vehicle-function identification module 804; a vehicle-function activation module 806; the like, or other, for example.

The processing hardware unit 706, executing the user-gesture determination module 802, determines which gesture a user has made based on user input data. The user input data can include one or multiple data components. The user input data is received to the processing hardware unit 706, executing the module 802, from one or more of a variety of data sources. Example data sources include one or more sensors of the physiological monitoring device 102 or other wearable device, worn by the user, and one or more other sensors, such as of the vehicle 10, configured and arranged to sense motion of one or more user body parts, such as a user arm, wrist, head, etc. The other wearable device includes a smart bracelet, ring, cufflink(s), belt attachment, shoe or boot (footwear) attachment, legwear, arm wear, clothing, headphones, headgear, hat or other headwear, eyeglasses, rings, sunglasses, or watch, as just a few examples.

Figure 10:
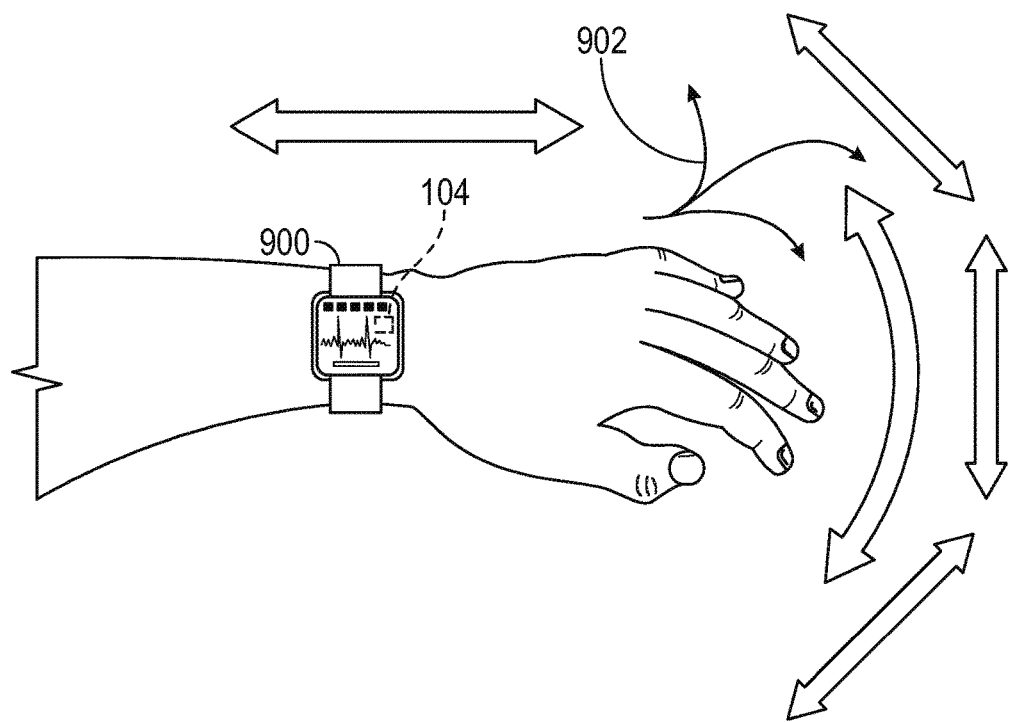
FIG. 10 illustrates an exemplary wearable device, worn on a user, and sample user motions, in accordance with various embodiments.

An example wearable device in the form of a smart bracelet is referenced by numeral 900 in FIG. 10. As referenced, the device 900 can be a computerized or electronic device having any components analogous to those shown in FIGS. 8 and 9—e.g., memory unit comprising executable instructions and a processing device for executing the instructions. Moreover, as discussed, the device 900 may be the physiological monitoring device 102 or may comprise one or more features of the physiological monitoring device 102, and thus, may include one or more physiological sensors 104.

In various embodiments, the device 900 includes at least one transmitter or transceiver components for at least sending signals or messages to the vehicle, such as signals or messages corresponding to user gestures and the physiological sensor signals. The transmitter/transceiver can have any of the qualities described above for the communication components of the physiological monitoring device 102, or other characteristics. The transmitter/transceiver can be configured, for instance, to communicate according to any of a wide variety of protocols, including BLUETOOTH®, infrared, infrared data association (IRDA), near field communications (NFC), the like, or improvements thereof.

And as referenced, the system(s) is in some embodiments configured to record—such as by one or more vehicle sensors sensing—user gestures, whether the user is wearing the device 900. As provided, the data source includes one or more sensors configured to sense motion of a user body part such as a wrist, head, arm, or hand. A user arm, wrist, and hand are shown in FIG. 10. The sensors can include but are not limited to including those described above in connection with the response sensors 39 of the physiological control system 100 of FIGS. 1 and 2, such as at least one camera 39' and/or sensing devices 40$a$, 40$b$ . . . 40$n$ of the sensor system 28 of the vehicle 10 (FIG. 1).

In various embodiments, the vehicle 10 and/or the device 900 is configured to determine whether the user is present or proximate the vehicle—such as by determining that the wearable device is proximate the vehicle 10. The vehicle 10 may identify or authenticate the user presence for this purpose in any of a variety of ways, along with or in addition to detecting proximity of a user mobile device, such as by voice authentication, facial authentication, retina scan, etc. In various embodiments, the device 900 and/or the vehicle 10 only sense and/or act on user gestures after the presence or proximity determination is made at the device 900 and/or vehicle 10.

The processing hardware unit 706 executing the vehicle-function activation module 806 performs the function(s) identified by the processing hardware unit 706 executing the prior modules 802, 804. Example functions including initiate a 911 call, locking or unlocking doors, etc.

Figure 11:
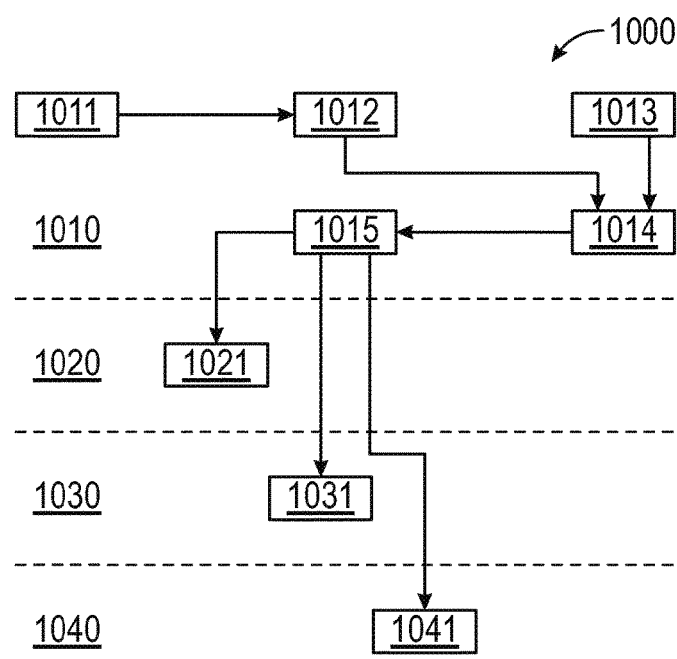
FIG. 11 illustrates an exemplary method, in accordance with various embodiments.

FIG. 11 shows exemplary methods 1000 according to embodiments of the present technology. It should be understood that the methods 1000 are not necessarily presented in any particular order and that performance of some or all the steps in an alternative order is possible and is contemplated. It should also be understood that the illustrated methods 1000 can be ended at any time.

In certain embodiments, some or all steps of the process (es) 1000 and/or substantially equivalent steps are performed by a processor, e.g., computer processor, executing computer-executable instructions stored or included on a computer-readable medium, such as the data storage device 704 of the computer-based system 700 described above.

The flow of the method 1000 is divided by way of example into four sections: a user personalization and input section 1010, a comfort/convenience vehicle function section 1020, a local alarm vehicle function section 1030, and a remote communication or alert section 1040.

At 1011, a user puts on or has the physiological monitoring device 102, as illustrated with the example device 900 of FIG. 10, or other mobile device, such as a smart phone. At 1012, sensor(s) and computing system(s) of the mobile device and/or subject vehicle teach and/or learn about user movements—e.g., gestures—and associated desired vehicle functions. One or more of these learned movements may be stored as a response setting in the response datastore 306. In various embodiments, the system can have default organization of gestures available to use, and/or the user can organize the gestures, such as by establishing in the system levels of interaction—e.g., a first level of convenience/comfort gestures; and a second level for emergency situations. Teachings can include suggesting gestures for the user to use to trigger corresponding vehicle functions. The suggestions can be communicated to the user from the vehicle by a user device or by the display 25a (FIG. 1). The suggestions can include standard, or default, gestures already associated with corresponding vehicle functions. The user selects one or more of these suggestions as the preference 368, which may be stored in the response datastore 306.

At 1013, the method adopts or defines default or personalized gesture controls based on user input, default programming, instructions or updates from the remote transportation system 52. At 1014, the method determines user disposition. The operation can include, for instance, determining that the user is approaching the vehicle 10, proximate the vehicle, in the vehicle, or exiting the vehicle 10.

At 1015, the method detects a user gesture or movement and identifies the gesture based on signals received from the response sensors 39. The method determines a vehicle function or vehicle response corresponding to the user movement. In various embodiments, the method retrieves the response setting 328 based on the identified gesture and sets the vehicle response or function based on the retrieved response setting 328.

At 1021, the method implements local convenient or comfort functions determined in the prior operation 1015. Example functions in this section 1020 include but are not limited to illuminating or blinking vehicle exterior lights (head lamps, tail lamps, turn signals, under vehicle-body lights and/or interior lights, door lock/unlock, or door, decklid, or trunk opening/closing, activating the conditions control module 312, dismissing the prompt 330, etc.

At 1031, the method implements local alert or emergency functions determined in the prior operation 1015. Example local functions here include actuating the vehicle horn, flashing exterior or interior lights, etc. In contemplated embodiments, the function includes the vehicle recording audio and/or video, such as to record a potential criminal situation involving or near the user. At 1041, the method implements extra-vehicle-related functions determined in the prior operation 1015. Example functions here include initiating a phone call, a text message, transmitting of GPs location or video, such as that recorded at 1031. The phone call can be to 911, can be an automated call in which the vehicle provides a message to the receiver, or can be a user call in which live audio is transmitted. In a contemplated embodiment, the function includes any user mobile device or nearby recording device, such as parking-lot infrastructure, recording audio and/or video, such as to record a potential criminal situation involving or near the user.

The method 1000 can end or any one or more operations of the method 1000 can be performed again.

Figure 12:
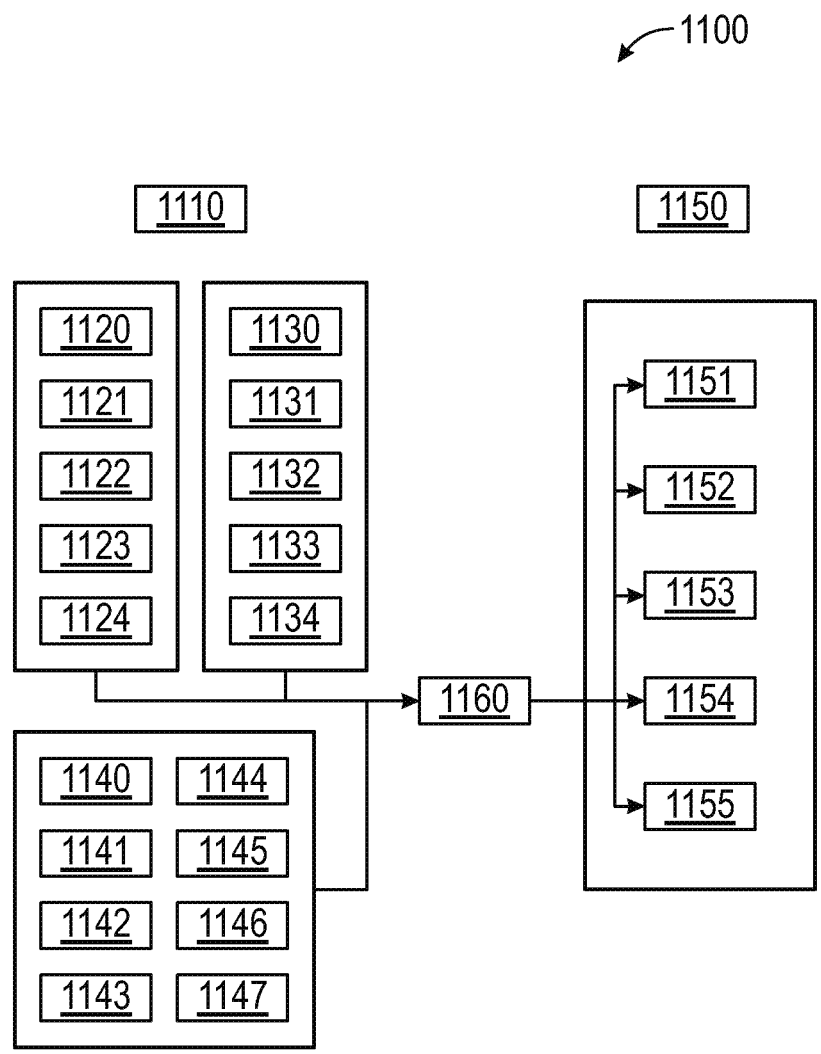
FIG. 12 illustrates exemplary system inputs and outputs, in accordance with various embodiments.

FIG. 12 shows an arrangement 1100 of example system inputs 1110 and outputs 1150 separated by a gesture recognition system 1160, according to embodiments of the present technology. The inputs 1110 can be divided into three primary types: user gestures 1120, off-board inputs 1130 (off-board of the vehicle), and on-board inputs 1140 (aboard the vehicle).

Example user gestures 1120 including any of those reference above, such as user body part rotation 1121, pointing or moving linearly 1122, swiping 1123, and clicking 1124. Example off-board inputs 1130 including inputs from one or more vehicle cameras 1141, other vehicle sensor(s) 1142, a Bluetooth input 1143 to the vehicle 10, a remote input 1144 to the vehicle 10, such as from the remote transportation system 52, input from a vehicle or mobile device application 1145, such as navigation or wearable location determining app, vehicle or vehicle-related controls or function inputs 1146, such as a user touch pad, vehicle lighting, keyfob, locking/unlocking button or actuation, keyfob, and vehicle location input 1147. Example on-board inputs 1140 include location information (e.g., GPS) or other data input from satellite 1131, cellular 1132, V2X 1133 (V2V, V2I, etc.), or data via the internet 1134, connected to in any suitable manner.

The gesture recognition system 1160 in various embodiments includes any of the components provided above in connection with gesture recognition functions, such as user mobile device or vehicle sensors and computing systems.

The output functions 1150 include but not limited to any of those described above, such as illumination of vehicle lights 1151, locking/unlocking of vehicle door locks 1152, actuating the vehicle horn 1153, initiating a communication 1154, such as a call or text message, or transmission 1155 of mobile device or vehicle location and/or audio or video recorded at the mobile device, vehicle, or nearby structure, such as a parking lot camera. In various embodiments, the output functions 1150 also include setting the gesture activation 365 for the conditions control module 312 and setting the response 324 for the physiological monitor module 304.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

What is claimed is:

1. A method for controlling a vehicle based on a physiological trait, comprising:
    receiving physiological data from one or more physiological sensors, the physiological data including at least one of a blood pressure, a pulse rate, a body temperature, a respiration rate, a blood sugar and a blood alcohol level;
    processing the received physiological data, by a processor, and determining, by the processor, one or more physiological conditions based on the received physiological data from the one or more physiological sensors;
    processing the received physiological data, by the processor, and determining, by the processor, one or more physiological changes based on a comparison of a baseline reading of the physiological data from the one or more physiological sensors and a subsequent reading of the physiological data from the one or more physiological sensors;

based on the determined one or more physiological changes, retrieving, by the processor, a setting associated with the determined one or more physiological changes and outputting, by the processor, one or more control signals to a vehicle system to control an operation of the vehicle system based on the setting associated with the determined one or more physiological changes;

outputting, by the processor, a prompt based on the determined one or more physiological conditions;

determining, by the processor, whether the prompt has been dismissed; and based on the determining that the prompt has not been dismissed, retrieving, by the processor, the setting associated with the determined one or more physiological conditions and outputting, by the processor, one or more control signals to a vehicle control system to operate the vehicle autonomously based on the setting associated with the determined one or more physiological conditions.

2. The method of claim 1, wherein the setting is a user defined setting or a predefined default setting.

3. The method of claim 1, further comprising:
outputting, by the processor, a message to an external authority system based on the determining that the prompt has not been dismissed.

4. The method of claim 1, further comprising:
outputting, by the processor, at least a notification and a GPS location of the vehicle based on the determining that the prompt has not been dismissed.

5. The method of claim 1, wherein the determining, by the processor, whether the prompt has been dismissed further comprises:
receiving sensor data from one or more response sensors;
processing the sensor data to determine whether a gesture has been made by the user to dismiss the prompt; and
determining the prompt has been dismissed based on the determination of the gesture.

6. The method of claim 1, wherein the outputting, by the processor, the prompt based on the determined one or more physiological conditions further comprises:
outputting, by the processor, a prompt to place the vehicle in autonomous drive mode.

7. The method of claim 1, wherein the outputting, by the processor, the prompt based on the determined one or more physiological conditions further comprises:
outputting, by the processor, a prompt to suggest a diversion from a planned route to rest or seek treatment and one or more locations to rest or seek treatment based on a location of the vehicle.

8. A system for controlling a vehicle based on a physiological trait, comprising:
a source of physiological data regarding a user of the vehicle, the physiological data observed by one or more physiological sensors and the physiological data including at least one of a blood pressure, a pulse rate, a body temperature, a respiration rate, a blood sugar and a blood alcohol level; and
a control module having a processor that:
processes the physiological data;
determines one or more physiological conditions based on the received physiological data from the one or more physiological sensors;
outputs one or more control signals to a vehicle control system to operate the vehicle autonomously based on the determined one or more physiological conditions;
determines one or more physiological changes based on a comparison of a baseline reading of the physiological data from the one or more physiological sensors and a subsequent reading of the physiological data from the one or more physiological sensors; and
outputs one or more control signals to the vehicle control system to command one or more of an HVAC system, a seat system, an infotainment system, a lock system, a light system, a window system and an alarm system based on the determined one or more physiological changes.

9. The system of claim 8, wherein the source of physiological data is a personal device associated with the user.

10. The system of claim 8, wherein the processor retrieves a setting associated with the determined one or more physiological changes, and outputs the one or more control signals to the vehicle control system based on the setting.

11. The system of claim 10, wherein the setting is a user defined setting or a predefined default setting.

12. The system of claim 8, wherein the processor outputs a prompt based on the determined one or more physiological conditions, determines whether a user response has been received to dismiss the prompt and the control module outputs the one or more control signals to the at least one vehicle control system based on a determination that the prompt has not been dismissed.

13. The system of claim 12, wherein the processor outputs at least a notification that the physiological data is outside of a predefined acceptable range and a GPS location of the vehicle based on the determination that the prompt has not been dismissed.

14. The system of claim 12, wherein the processor outputs a message to an external authority system based on the determination that the prompt has not been dismissed.

15. The system of claim 12, wherein the processor determines whether the user response has been received based on sensor data received from one or more response sensors, and the processor processes the sensor data to determine whether a gesture has been made by the user, and determines whether the user response has been received to dismiss the prompt based on the determination of the gesture.

16. A wearable physiological device, comprising:
at least one physiological sensor that observes at least one of a blood pressure, a body temperature, a respiration rate, a blood sugar and a blood alcohol level associated with a wearer of the physiological device and generates sensor signals based thereon; and
a control module having a processor that processes the sensor signals and outputs the sensor signals to a system associated with a vehicle to control a vehicle system based on the sensor signals.

17. The wearable physiological device of claim 16, wherein the wearable physiological device is a portable electronic device selected from the group comprising: a watch, a ring, an earring, a bracelet, a cufflink, a necklace, a tie, glasses, chest band, smart clothes and combinations thereof.

* * * * *